US011779239B2

(12) United States Patent
Buesseler et al.

(10) Patent No.: US 11,779,239 B2
(45) Date of Patent: Oct. 10, 2023

(54) CORE DESIGNS FOR MINIATURE INDUCTIVE COIL SENSORS

(71) Applicant: St. Jude Medical International Holding S.àr.l., Luxembourg (LU)

(72) Inventors: Ryan K. Buesseler, Bristow, VA (US); Bruce Ebner, Shorewood, MN (US)

(73) Assignee: ST. JUDE MEDICAL INTERNATIONAL HOLDING S.À R.L., Luxembourg (LU)

( * ) Notice: Subject to any disclaimer, the term of this patent is extended or adjusted under 35 U.S.C. 154(b) by 743 days.

(21) Appl. No.: 16/329,532

(22) PCT Filed: Jul. 26, 2017

(86) PCT No.: PCT/IB2017/054548
§ 371 (c)(1),
(2) Date: Feb. 28, 2019

(87) PCT Pub. No.: WO2018/042271
PCT Pub. Date: Mar. 8, 2018

(65) Prior Publication Data
US 2019/0223756 A1 Jul. 25, 2019

Related U.S. Application Data

(60) Provisional application No. 62/382,708, filed on Sep. 1, 2016.

(51) Int. Cl.
*A61B 5/06* (2006.01)
*H01F 17/04* (2006.01)
(Continued)

(52) U.S. Cl.
CPC ........... *A61B 5/062* (2013.01); *G01D 5/2013* (2013.01); *H01F 17/045* (2013.01);
(Continued)

(58) Field of Classification Search
CPC ........ G01D 5/2013; G01D 5/20; G01D 5/202; G01D 5/204; G01D 5/2046; G01D 5/2086; A61B 5/062
See application file for complete search history.

(56) References Cited

U.S. PATENT DOCUMENTS

| 5,358,514 A | 10/1994 | Schulman et al. |
| 7,197,354 B2 | 3/2007 | Sobe |

(Continued)

FOREIGN PATENT DOCUMENTS

WO 2016149388 A1 9/2016

OTHER PUBLICATIONS

Tumanski, Slawomir, Induction coil sensors—A review, Measurement Science & Technology (2007)—Meas Sci Technol. 18. 10.1088/0957-0233/18/3/R01.

*Primary Examiner* — Boniface Ngathi
*Assistant Examiner* — Milton Truong
(74) *Attorney, Agent, or Firm* — Billion & Armitage

(57) ABSTRACT

A position sensor used in medical devices for use with medical positioning systems. The position sensor includes a core (80) having a body and one or more projections (841,842) extending from the body, wherein the core comprises a high-permeability material. The position sensor further includes a coil (74) surrounding the body, wherein the coil is configured to generate a voltage when subject to a magnetic field. The one or more projections extending from the body of the core are configured to concentrate the magnetic field into the coil and increase the voltage. Thus, various core designs are described which have projections which may increase the electrical and/or mechanical integrity of the position sensor and/or which may also induce magnetic flux flow within the position sensor thereby increasing the signals generated by the position sensor.

18 Claims, 24 Drawing Sheets

(51) Int. Cl.
*G01D 5/20* (2006.01)
*H01F 27/29* (2006.01)
*H01F 27/255* (2006.01)
*H01F 27/28* (2006.01)

(52) U.S. Cl.
CPC ....... *H01F 27/255* (2013.01); *H01F 27/2828* (2013.01); *H01F 27/29* (2013.01); *A61B 2562/0223* (2013.01)

(56) References Cited

U.S. PATENT DOCUMENTS

| | | |
|---|---|---|
| 7,386,339 B2 | 6/2008 | Strommer et al. |
| 8,858,468 B2 | 10/2014 | Sela et al. |
| 8,979,837 B2 | 3/2015 | de la Rama et al. |
| 9,364,640 B2 | 6/2016 | Vanney et al. |
| 2004/0252002 A1* | 12/2004 | Barlian .................. H01F 38/14 336/198 |
| 2005/0707790 | 3/2005 | Niwa et al. |
| 2006/0066498 A1* | 3/2006 | Abe ....................... H01Q 1/273 343/788 |
| 2009/0278689 A1 | 11/2009 | Gisselberg et al. |
| 2010/0152731 A1 | 6/2010 | de la Rama et al. |
| 2010/0321015 A1* | 12/2010 | Susel ....................... H01F 5/04 324/258 |
| 2011/0098559 A1* | 4/2011 | Besz .................. A61B 17/3403 600/424 |
| 2011/0166455 A1* | 7/2011 | Cully ................... A61B 8/4466 600/463 |
| 2011/0313417 A1 | 12/2011 | de la Rama et al. |
| 2013/0066194 A1 | 3/2013 | Seter et al. |
| 2014/0039258 A1 | 2/2014 | Sekiguchi et al. |
| 2014/0200556 A1 | 7/2014 | Sela et al. |
| 2015/0374254 A1 | 12/2015 | Sobe |
| 2016/0113729 A1* | 4/2016 | Burg ....................... H05K 1/028 600/424 |
| 2016/0235338 A1* | 8/2016 | Sekiguchi .......... A61B 1/00043 |
| 2016/0276739 A1 | 9/2016 | Buesseler et al. |
| 2016/0310041 A1* | 10/2016 | Jenkins ................ A61B 5/6851 |

* cited by examiner

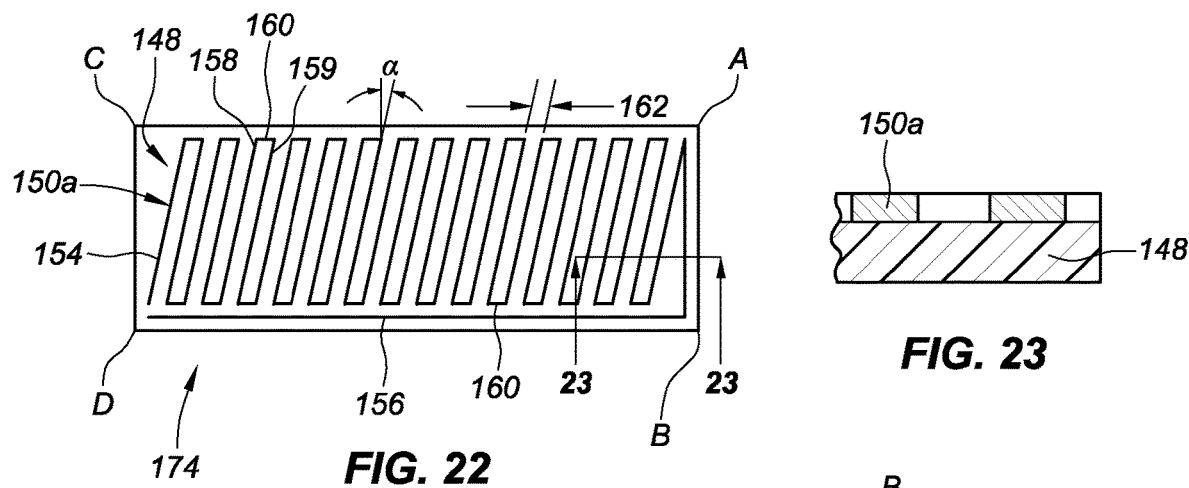
FIG. 22
FIG. 23
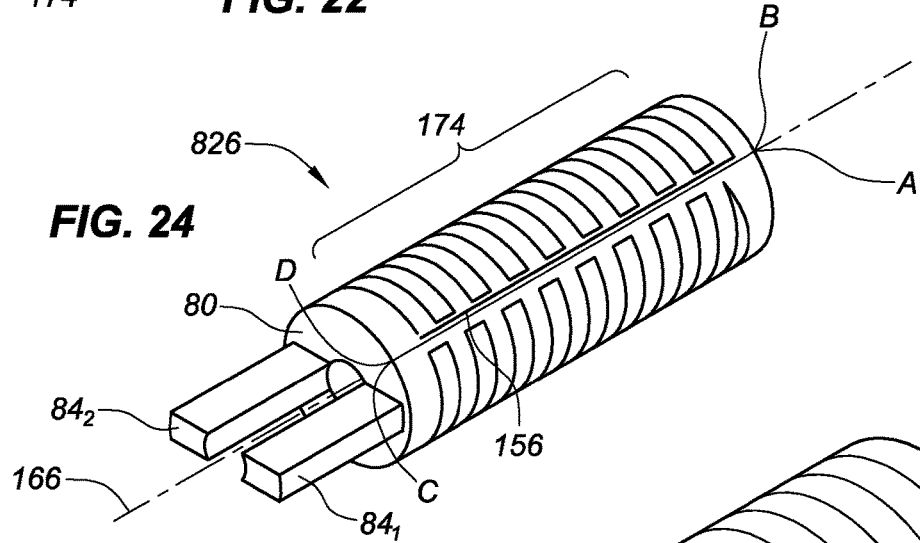
FIG. 24
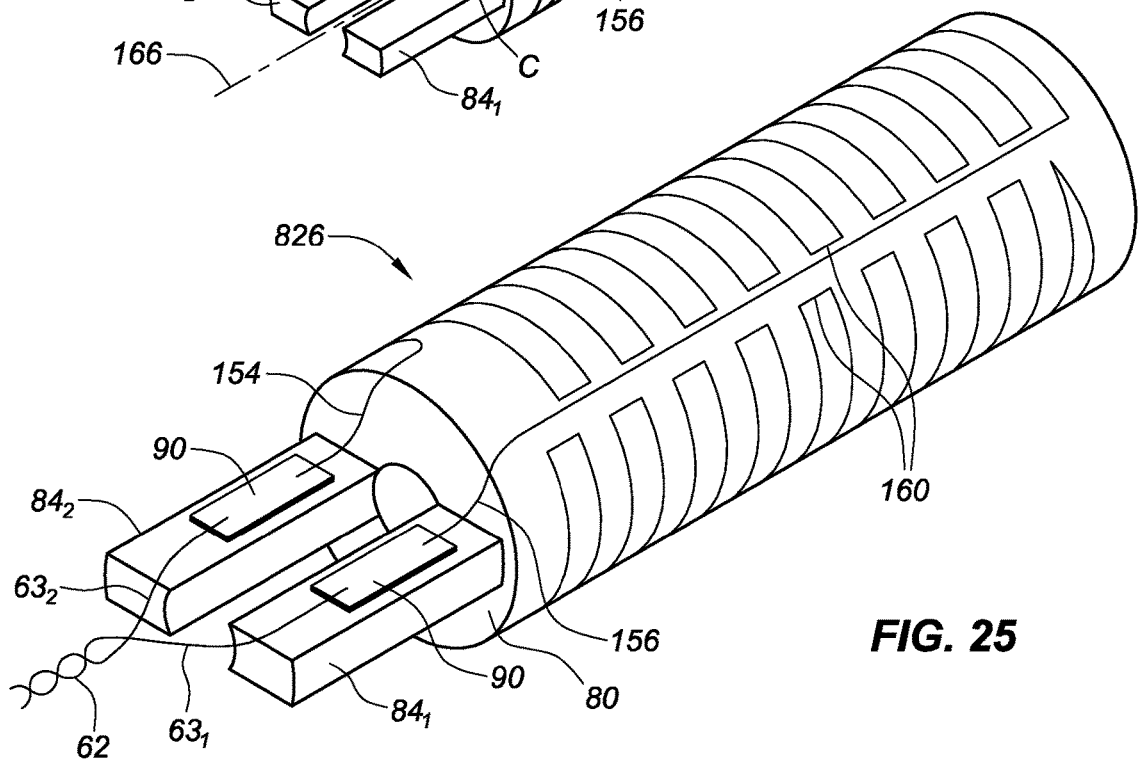
FIG. 25

CORE DESIGNS FOR MINIATURE INDUCTIVE COIL SENSORS

CROSS-REFERENCE TO RELATED APPLICATIONS

This application is a United States national stage application of International application no. PCT/IB2017/054548, filed 26 Jul. 2017 and published under International publication no. WO 2018/042271 A1 on 8 Mar. 2018 (the '548 application). This application claims priority to U.S. provisional patent application No. 62/382,708, filed 1 Sep. 2016 (the '708 application). The '548 application and the '708 application are both hereby incorporated by reference as though fully set forth herein.

BACKGROUND a. Field

The instant disclosure relates to magnetic sensors, such as those used in medical positioning systems. In one embodiment, the instant disclosure relates to core designs for increasing the signal strength of magnetic sensors.

b. Background Art

Medical positioning systems have the capability of tracking a medical device within a known three-dimensional tracking space. Typical medical devices used with medical positioning systems include catheters, introducers, guide wires and the like. Each of these medical devices may use elongate, flexible shafts on which various operational elements, such as electrodes, are used to perform various diagnosis or treatment procedures, such as mapping and ablation, on anatomy, such as the heart.

Some types of medical positioning systems utilize a plurality of magnetic fields to induce a voltage in a position sensor having one or more coils in order to determine the location of that sensor within a three-dimensional space defined by the magnetic fields. The voltage induced in such sensors or search coils can be measured by an electronic control unit as a signal indicative of the location of the sensor. The reliability and accuracy of the magnetic positioning system is related to the dependability of the sensor signal. As such, it is beneficial to increase the strength of the voltage induced in the coil.

One method of increasing the output strength of the sensor is to position a high-permeability core within the coil winding to increase the electric voltage generated by the coil. The presence of the core increases the magnetic flux density by drawing magnetic field lines toward the sensor. Once such sensor coil and core combination is described in U.S. Pat. No. 7,197,354 to Sobe, entitled "System for Determining the Position and Orientation of a Catheter."

The effectiveness of prior art cores may be limited by the geometry of the sensor and the medical device into which it is installed. For a medical device having an elongate, flexible shaft, it is desirable that the device have a small diameter, e.g., less than 19 French (approximately 6.33 millimeters), so as to enable movement through the vasculature. Sensors used within typical medical devices can be even smaller, on the order of 1 French (0.33 millimeters) or less. As such, the spaces available for the position sensor within the medical device and the core within the sensor are small.

The foregoing discussion is intended only to illustrate the present field and should not be taken as a disavowal of claim scope.

BRIEF SUMMARY

The instant disclosure relates to position sensors or search coils used in medical devices for use with medical positioning systems. Such medical devices may comprise mapping and ablation catheters for diagnosing and treating cardiac arrhythmias via, for example, radio frequency (RF) ablation. In particular, the instant disclosure relates to core designs having projections which may increase the electrical and/or mechanical integrity of a position sensor and/or which may also induce magnetic flux flow within the position sensor thereby increasing the signals generated by the position sensor. That is, the instant disclosure relates to core designs which allow for both signal amplification and electrical connection (e.g. solder joint) protection on an extremely small magnetic position sensor. The core designs described herein provide increased signal strength without sacrificing space.

In one embodiment, a position sensor for a medical device comprises a core comprising a body and one or more projections extending from the body. The position sensor further comprises a coil surrounding the body, wherein the coil is configured to generate a voltage when subject to a magnetic field.

In another embodiment, a position sensor for a medical device comprises a core comprising a body and one or more projections extending from the body, wherein the core comprises a high-permeability material. The position sensor further comprises a coil surrounding the body, wherein the coil is configured to generate a voltage when subject to a magnetic field. The one or more projections extending from the body of the core are configured to concentrate the magnetic field into the coil and increase the voltage.

In yet another embodiment, a medical device configured for diagnosis or treatment of a tissue within a body comprises an elongate member, a position sensor, and a conductor. The elongate member is configured to be received within the body and the elongate member has a proximal end and a distal end. The position sensor is disposed within the elongate member proximate the distal end of the elongate member. The position sensor comprises a core comprising a body and one or more projections extending from the body, and a coil surrounding the body, wherein the coil is configured to generate a voltage when subject to a magnetic field. The conductor is disposed within the elongate member extending from the position sensor to the proximal end of the elongate member.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 16 is an isometric view of a core having a body and projections extending therefrom according to another embodiment of the disclosure.

FIG. 22 is a top view of a printed coil formed using flexible printed circuitry for use in the embodiments of magnetic position sensors described herein.

FIG. 23 is a fragmentary, cross-sectional view of a portion of the printed coil illustrated in FIG. 22 taken along line 23-23.

FIG. 24 is an isometric view of a magnetic position sensor utilizing the printed coil illustrated in FIGS. 22 and 23 according to another embodiment of the disclosure.

FIG. 25 is a detailed isometric view of the magnetic position sensor utilizing the printed coil illustrated in FIG. 24.

DETAILED DESCRIPTION OF EMBODIMENTS

Several embodiments of core designs for magnetic position sensors are disclosed herein. In general, these core designs have field concentrating antennas are used in medical devices to increase the output signal of position sensors used in conjunction with medical positioning systems, particularly magnetic positioning systems. In one embodiment, the core designs help produce high gain induction sensors that can be used within medical devices used in conjunction with magnetic medical positioning systems. In other embodiments, the core designs provide a landing area for locating an electrical connection of the coil of the magnetic position sensor which may help increase the electrical and/or mechanical integrity of a position sensor. Details of the various embodiments of the present disclosure are described below with specific reference to the figures.

Figure 1:
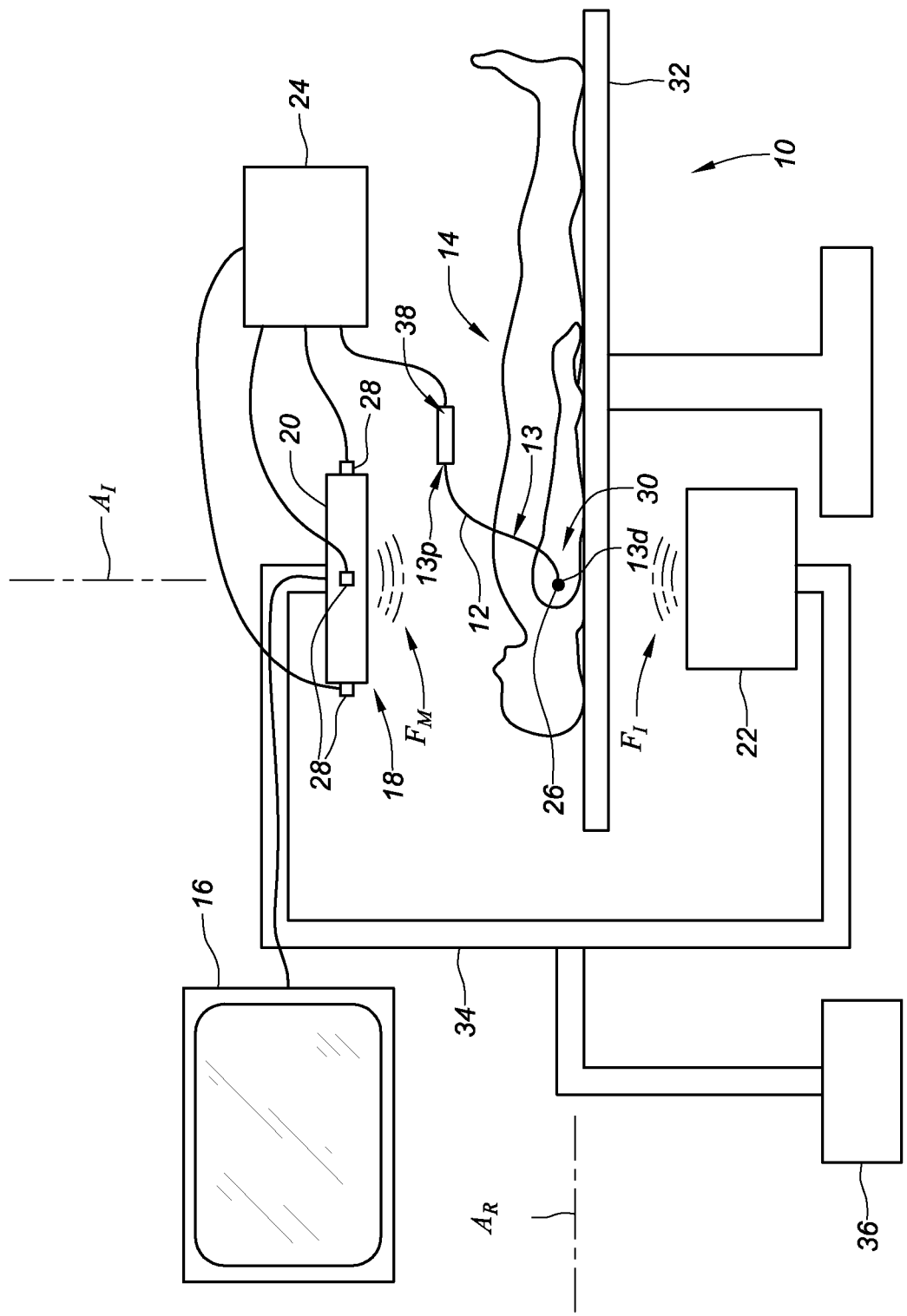
FIG. 1 is a schematic representation of a medical imaging system for generating and displaying data on a display screen using a medical device having a position sensor.

FIG. 1 is a schematic representation of medical imaging system 10 for determining the position of at least a portion of a medical device 12 (e.g., catheter, introducer, guidewire, and the like) relative to a model or an image of an organ of patient 14, as well as for generating and displaying the model and related information on display unit 16. System 10 includes moving imager 18, which includes intensifier 20 and emitter 22, and magnetic positioning system (MPS) 24, which includes position sensor 26 and field generators 28. Electrophysiology map information and cardiac mechanical activation data pertaining to the model generated by medical imaging system 10 is displayed on computer display 16 to facilitate diagnosis and treatment of patient 14. The present disclosure describes, among other things, a way to increase the signal output of a position sensor located within medical device 12 so that system 10 is better able to process data collected by medical device 12. For example, medical device 12 may include a coil in which a voltage is induced by the presence of a magnetic field generated by magnetic positioning system 24. The ability of the coil to interact with the magnetic field, and thereby generate current, is increased with the use of the field concentrating antennas of the present disclosure.

Moving imager 18 is a device which acquires an image of region of interest 30 while patient 14 lies on operation table 32. Intensifier 20 and emitter 22 are mounted on C-arm 34, which is positioned using moving mechanism 36. In one embodiment, moving imager 18 comprises a fluoroscopic or X-ray type imaging system that generates a two-dimensional (2D) image of the heart of patient 14.

Magnetic positioning system 24 includes a plurality of magnetic field generators 28 and medical device 12 having an elongate member 13, to which position sensor 26 is mounted proximate a distal end portion 13d of elongate member 13 and handle 38 is connected at a proximal end portion 13p of elongate member 13. MPS 24 determines the position of the distal portion of medical device 12 in a magnetic coordinate system generated by field generators 28, according to output of position sensor 26. In one embodiment, MPS 24 comprises a MediGuide gMPS magnetic positioning system, as is commercially offered by St. Jude Medical, Inc., that simultaneously generates a three-dimensional (3D) model of the heart of patient 14.

C-arm 34 positions intensifier 20 above patient 14 and emitter 22 underneath operation table 32. Emitter 22 generates, and intensifier 20 receives, an imaging field $F_1$, e.g., a radiation field, that generates a 2D image of area of interest 30 on display 16. Intensifier 20 and emitter 22 of moving imager 18 are connected by C-arm 34 so as to be disposed at opposite sides of patient 14 along imaging axis $A_I$, which extends vertically with reference to FIG. 1 in the described embodiment. Moving mechanism 36 rotates C-arm 34 about rotation axis $A_R$, which extends horizontally with reference to FIG. 1 in the described embodiment. Moving mechanism 36 or an additional moving mechanism may be used to move C-arm 34 into other orientations. For example, C-arm 34 can be rotated about an axis (not shown) extending into the plane of FIG. 1 such that imaging axis $A_I$ is rotatable in the plane of FIG. 1. As such, moving imager 18 is associated with 3D optical coordinate system having x-axis $X_I$, y-axis $Y_I$, and z-axis $Z_I$.

Magnetic positioning system (MPS) 24 is positioned to allow medical device 12 and field generators 28 to interact with system 10 through the use of appropriate wired and/or wireless technology. Medical device 12 is inserted into the vasculature of patient 14 such that position sensor 26 is located at area of interest 30. Field generators 28 are mounted to intensifier 20 so as to be capable of generating magnetic field $F_M$ in area of interest 30 coextensive with imaging field $F_1$. MPS 24 is able to detect the presence of position sensor 26 within the magnetic field $F_M$. In one embodiment, position sensor 26 may include three mutually orthogonal coils, as described in U.S. Pat. No. 6,233,476 to Strommer et al., the entire content of which is incorporated herein by reference in its entirety for all purposes and as though fully set forth herein. As such, magnetic positioning system 24 is associated with a 3D magnetic coordinate system having x-axis $X_P$, y-axis $Y_P$, and z-axis $Z_P$.

The 3D optical coordinate system and the 3D magnetic coordinate system are independent of each other, that is, they have different scales, origins, and orientations. Movement of C-arm 34 via moving mechanism 36 allows imaging field $F_I$ and magnetic field $F_M$ to move relative to area of interest 30 within their respective coordinate system. However, field generators 28 are located on intensifier 20 so as to register the coordinate systems associated with moving imager 18 and MPS 24. Thus, images generated within each coordinate system can be merged into a single image shown on display unit 16. Moving imager 18 and MPS 24 may function together as is described in U. S. Pub. No. US 2008/0183071 to Strommer et al., the entire content of which is incorporated herein by reference in its entirety for all purposes and as though fully set forth herein.

Display unit 16 is coupled with intensifier 20. Emitter 22 transmits radiation that passes through patient 14. The radiation is detected by intensifier 20 as a representation of the anatomy of area of interest 30. An image representing area of interest 30 is generated on display unit 16, including an image of medical device 12. C-arm 34 can be moved to obtain multiple 2D images of area of interest 30, each of which can be shown as a 2D image on display unit 16.

Display unit 16 is coupled to MPS 24. Field generators 28 transmit magnetic fields that are mutually orthogonal, corresponding to axes of the 3D magnetic coordinate system. Position sensor 26 detects the magnetic fields generated by field generators 28. The detected signals are related to the position and orientation of the distal end of medical device 12 by, for example, the Biot Savart law, known in the art. Thus, the precise position and location of the distal end of medical device 12 is obtained by MPS 24 and can be shown in conjunction with the 2D images of area of interest 30 at display unit 16. Furthermore, data from position sensor 26 can be used to generate a 3D model of area of interest 30, as is described in U.S. Pat. No. 7,386,339 to Strommer et al., the entire content of which is incorporated herein by reference in its entirety for all purposes and as though fully set forth herein.

Figure 2:
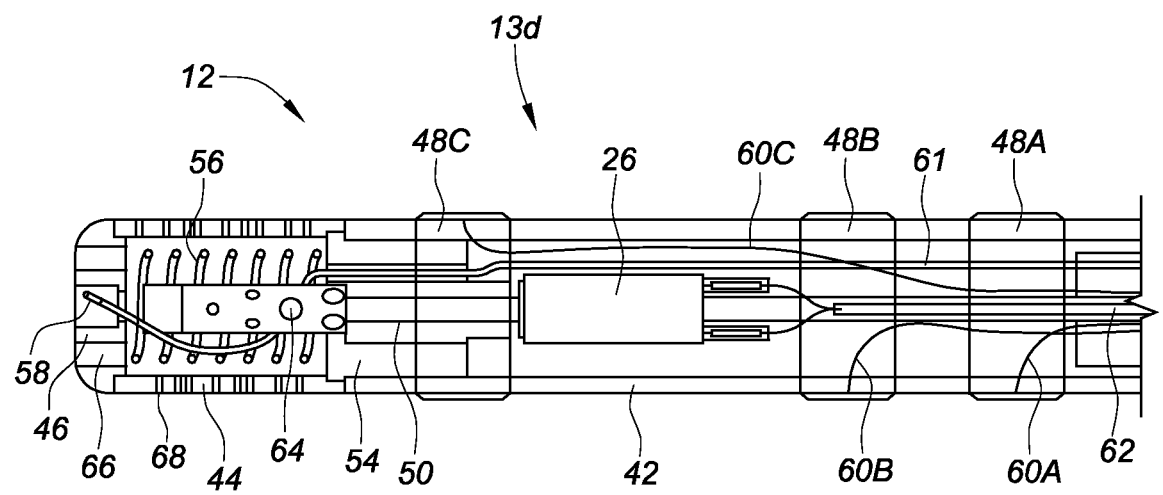
FIG. 2 is a partial cross-sectional view of a distal portion of the medical device of FIG. 1 showing a magnetic position sensor according to one embodiment of the disclosure.

FIG. 2 is a partial cross-sectional view of the distal end portion 13d of elongate member 13 of medical device 12 (shown as an ablation catheter for example only and without limitation) of FIG. 1 showing position sensor 26. Medical device 12 also includes an elongate member or sheath 42 extending from the proximal end portion 13p of elongate member 13 of medical device 12 to the distal end portion 13d of elongate member 13 of medical device 12, flexible tip 44, tip cap 46, electrodes 48A, 48B and 48C, fluid tube 50, plug 54, spring coil 56, and thermocouple 58.

Tube 50 is disposed concentrically within sheath 42 and is attached therein by an adhesive or the like. Tube 50 may be a PEEK tube or it may be made of other suitable nonconductive materials. Plug 54 is positioned around tube 50 to maintain tube 50 centered within sheath 42 and to facilitate joining of flexible tip 44 to sheath 42. For example, flexible tip 44 may be metallurgically joined to plug 54 at a flange. Flexible tip 44 includes incisions that allow flexible tip 44 to bend. Spring coil 56 is supported between tip cap 46 and plug 54 surrounding tube 50 and provides structural integrity to sheath 42 and resiliently maintains flexible tip 44 in a predetermined configuration when at rest and no force is placed on flexible tip 44. In the embodiment shown, the predetermined rest configuration orients the longitudinal axis of flexible tip 44 to follow a straight line coincident with a central axis of medical device 12.

Band electrodes 48A and 48B are provided on sheath 42 and may be used for diagnostic purposes or the like. Band electrode 48C is provided on sheath 42 and may be used for ablating tissue. Conductor wires 60A, 60B and 60C are provided to connect electrodes 48A, 48B and 48C, respectively, to the proximal portion of medical device 12, such as handle 38, for ultimate connection with MPS 24 and system 10. Thermocouple 58 is disposed in tip cap 46 and may be supported by an adhesive. Conductor wire 61 connects thermocouple 58 to the proximal portion of medical device 12, such as handle 38.

Position sensor 26 circumscribes tube 50 within sheath 42. As described in greater detail elsewhere herein, position sensor 26 comprises a conductor coil that is receptive to magnetic fields. Position sensor 26 is electrically connected to conductor 62 to connect to the proximal portion of medical device 12, such as handle 38. Conductor 62 may comprise a pair of conductors which extend within medical device 12 to proximal end portion 13p or elongate member 13. Conductor 62 may comprise an unshielded twisted-pair (TP) cable or alternately a shielded twisted-pair cable, or any other functionally equivalent signal cable known in the art. One or more of polymer, PTFE, and/or other appropriate materials may be included in conductor 62 for electrical insulation purposes.

In operation, medical device 12 is inserted into the vasculature of a patient such that flexible tip 44 is located at an area where it is desirable to perform a medical procedure (e.g., near tissue that is to be ablated). Ablation energy (e.g., RF energy) could then be delivered through tip cap 46, flexible tip 44, and/or one or more of band electrodes 48A, 48B, and 48C. Flexible tip 44 is able to bend so as to allow, for example, band electrode 48C to contact the tissue with a reduced risk of puncturing or otherwise damaging the tissue. As mentioned, band electrodes 48A, 48B, and 48C may be used to gather physiological data from the patient.

Tube 50 allows an irrigation fluid to be conveyed to the ablation site in order to control the temperature of the tissue and remove impurities from the site. For example, irrigation fluid from an external storage tank may be connected to handle 38 whereby the fluid is introduced, e.g. pumped, into tube 50. Tube 50 is provided with (or is affixed to a distal component that is provide with) radial ports 64 to allow fluid to escape tube 50. Fluid is permitted to escape medical device 12 at tip ports 66 in tip cap 46 and ports 68 in flexible tip 44 formed by the noted incisions. Thermocouple 58 permits operators of system 10 to monitor the temperature of or near the ablation site.

Position sensor 26 allows for accurate placement of, for example, band electrode 48C within the patient. Additional details of the construction of sheath 42, flexible tip 44, fluid tube 50, spring coil 56, and other components of medical device 12 can be found in, for example, U. S. Pub. No. US 2010/0152731, now U.S. Pat. No. 8,979,837, and U. S. Pub. No. US 2011/0313417, both to de la Rama et al., the entire contents of which are incorporated herein by reference in its entirety for all purposes and as though fully set forth herein. Additional details of the construction of position sensor 26 and other components can be found in U. S. Pub. No. US 2014/0200556 to Sela et al., the entire contents of both of which are incorporated herein by reference in their entirety for all purposes and as though fully set forth herein. Medical device 12 may further include pull wires for aiding navigation of medical device 12, as is known in the art.

Figure 3:
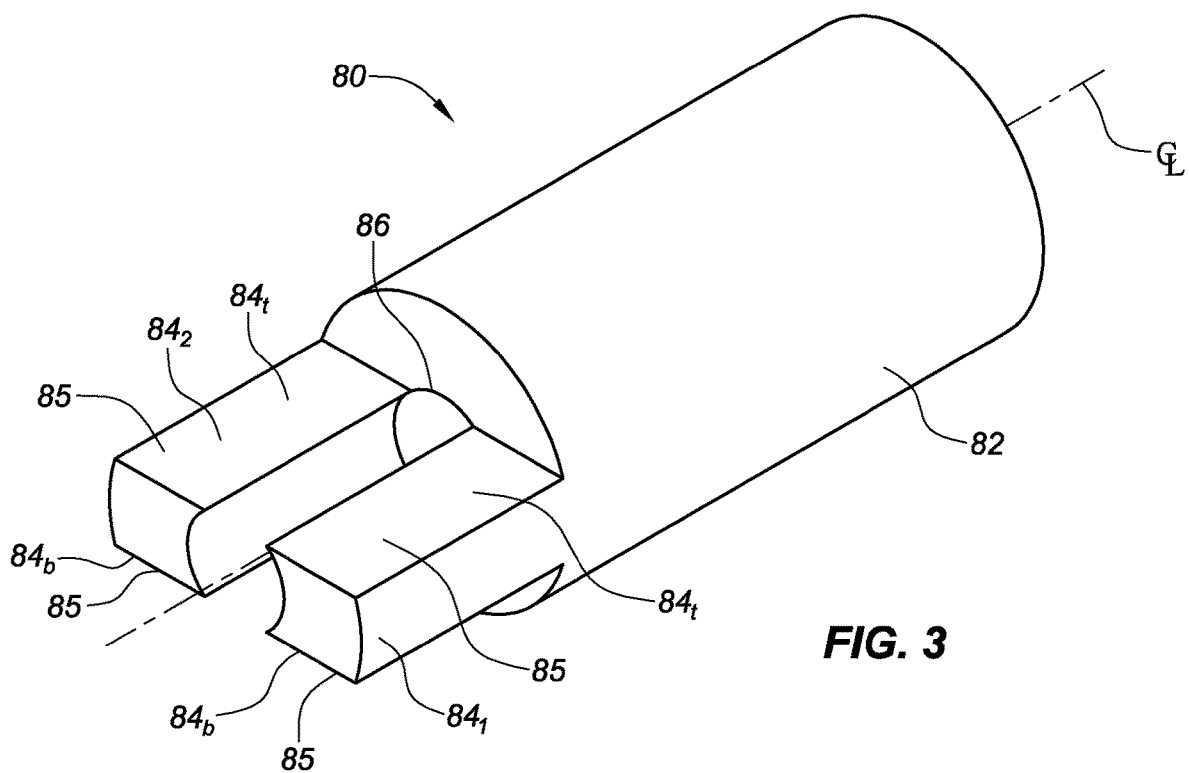
FIG. 3 is an isometric view of a core having a body and projections extending therefrom according to one embodiment of the disclosure.

FIG. 3 is an isometric view of core 80 for use in magnetic position sensor 26. In the embodiment shown, core 80 comprises a body 82 from which one or more projections $84_1$, $84_2$ extend therefrom. Projections $84_1$, $84_2$ extend away from body 82 parallel to center line $C_L$ of core 80. In various embodiments, core 80 comprises an annular core constructed of high permeability material, such as those described in the aforementioned U.S. Pat. No. 7,197,354 to Sobe, the entire content of which is incorporated herein by reference in its entirety for all purposes and as though fully set forth herein. Core 80 may include a lumen 86 extending through the axial length of core 80 along the longitudinal axis or center line $C_L$ of core 80. Core 80 is desirably shaped as a cylinder, having a circular shape in radial cross section; however, it will be understood that other shapes are possible (e.g., oval shape in radial cross section). For example only and without limitation, body 82 and projections $84_1$, $84_2$ may be manufactured from a single core blank. Projections $84_1$, $84_2$ may be manufactured through a variety of manufacturing techniques including, but not limited to, machining, electrical discharge machining (EDM), laser EDM, and additive manufacturing techniques including, but not limited to, 3D printing and laser sintering. Projections $84_1$, $84_2$ may be integrally formed as a part of core 80. Projections $84_1$, $84_2$ are rigidly fixed with respect to body 82 of core 80. Accordingly, any movement between projections $84_1$, $84_2$ and body 80 is reduced or eliminated.

In various embodiments (for example only and without limitation), body 82 of core 80 may be from about 0.5 mm to about 5 mm in length (e.g., about 0.5 mm, about 1.0 mm, about 1.5 mm, about 2.0 mm, about 2.5 mm, about 3.0 mm, about 3.5 mm, about 4.0 mm, about 4.5 mm, about 5.0 mm). In other embodiments (for example only and without limitation), body 82 of core 80 may be less than about 0.5 mm in length. In other embodiments (for example only and without limitation), body 82 of core 80 may be greater than about 5 mm in length. In an exemplary embodiment, body 82 of core 80 is about 2 mm in length. In various embodiments (for example only and without limitation), projections $84_1$, $84_2$ may be from about 0.05 mm to about 2 mm in length (e.g., about 0.05 mm, about 0.1 mm, about 1.0 mm, about 1.5 mm, about 2.0 mm). In other embodiments (for example only and without limitation), projections $84_1$, $84_2$ may be less than about 0.05 mm in length. In other embodiments (for example only and without limitation), projections $84_1$, $84_2$ may be greater than about 2 mm in length. In an exemplary embodiment, projections $84_1$, $84_2$ are about 1 mm in length. In various embodiments (for example only and without limitation), each projection $84_1$, $84_2$ has the same length, while in other embodiments, projections $84_1$, $84_2$ have different lengths. Although projections $84_1$, $84_2$ are shown extending proximally from body 82, it will be understood that projections $84_1$, $84_2$ could extend distally from body 82, or extend both proximally and distally from body 82 without departing from the scope of the disclosure. That is projections $84_1$, $84_2$ could extend from either end or both ends of body 82 of core.

As described in greater detail below, projections $84_1$, $84_2$ increase the signal generated by position sensor 26 to increase the accuracy of the location data. That is, projections $84_1$, $84_2$ funnel or concentrate magnetic flux into position sensor 26 to increase the voltage generated within the coil winding of position sensor 26. Therefore, the voltage output of position sensor 26 is increased by the inclusion one or more projections $84_1$, $84_2$ extending from core 80 wherein core 80 is constructed of a high magnetic permeable material to increase magnetic field interaction with the position sensor. Increased voltage output of the position sensor increases the signal generated by the position sensor that is interpreted by MPS 24 and system 10. Improved signal strength can improve the accuracy of the placement of medical device 12 relative to the anatomy generated by emitter 22 and intensifier 20 on display screen 16, such as by increasing the signal-to-noise ratio of MPS 24. Furthermore, hardware used within system 10 may be able to use larger amplification levels and magnetic transmission frequencies.

This is beneficial as it lowers the environmental influence to magnetic transmitters, which drives down positional error. Improved signal strength also permits smaller form factors for the design of the sensor, while maintaining the same signal output.

Figure 4:
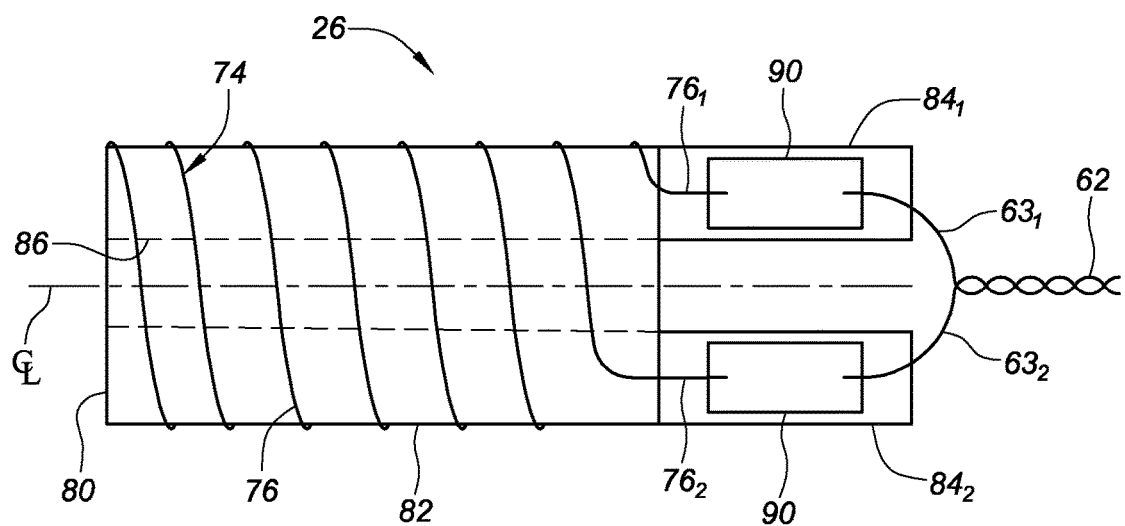
FIG. 4 is a top view of a magnetic position sensor according to one embodiment of the disclosure having the core illustrated in FIG. 3.
Figure 5:
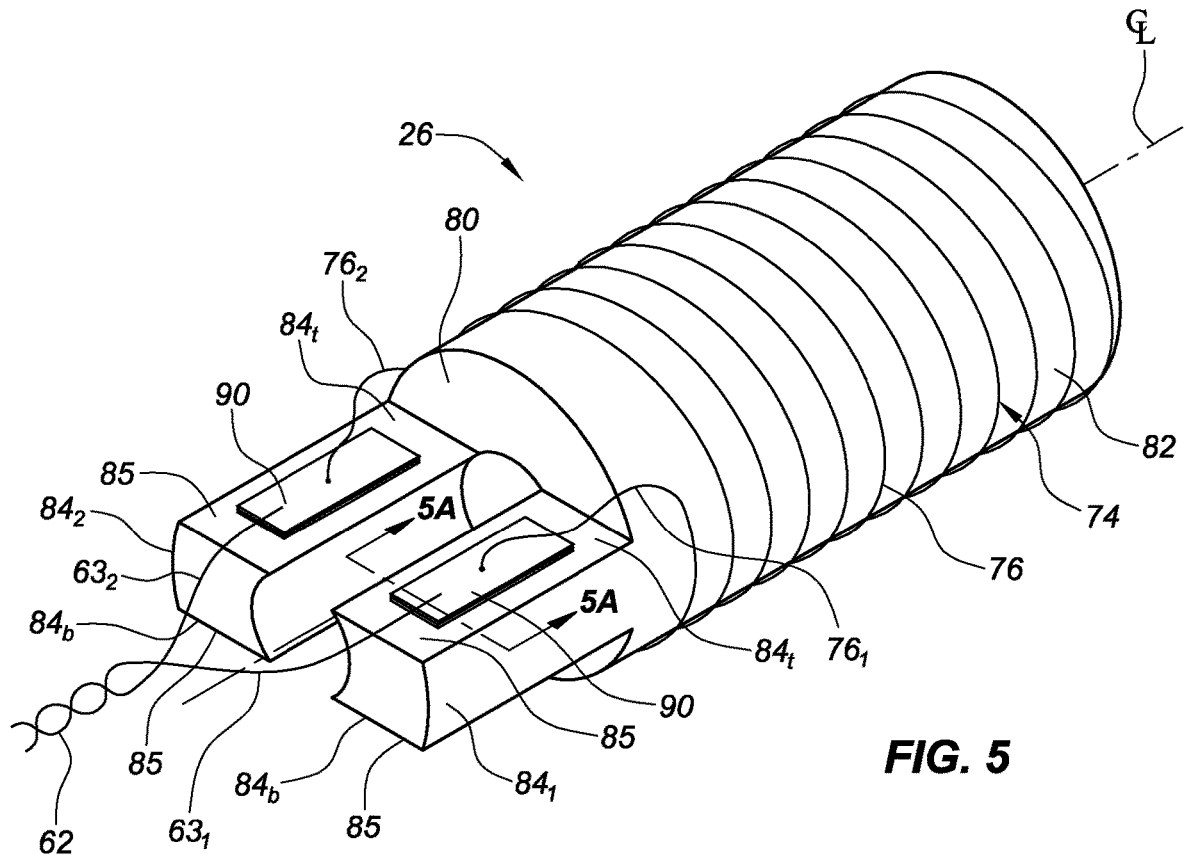
FIG. 5 is an isometric view of the magnetic position sensor illustrated in FIG. 4.

As shown in FIGS. 4 and 5, position sensor 26, further comprises coil 74 surrounding core 80. Coil 74 of position sensor 26 may be formed from a length of conductive wire 76, such as copper, spirally wound about center line $C_L$ of core 80. Coil 74 generally only surrounds body 82 of core 80 with projections $84_1$, $84_2$ not being surrounded by coil 74. In an exemplary embodiment, for example only and without limitation, core 80 is made of a hollow tube of dimensions 0.003" ID×0.007" OD (0.0762 mm ID×0.1778 mm), and body 82 is 2 mm long and projections $84_1$, $84_2$ extend 1 mm from body 82. Four layers of 58 AWG wire (0.0004" OD) (0.01016 mm OD) is wound around body 82 of core 80 to form coil 74. Leads $76_1$, $76_2$ of coil 74 terminate on projections $84_1$, $84_2$, respectively, where leads $76_1$, $76_2$ make an electrical connection with leads $63_1$, $63_2$, respectively, of conductor 62 (shown as a twisted pair in FIG. 4). In an exemplary embodiment, for example only and without limitation, leads $63_1$, $63_2$, respectively, of conductor 62 may be 50 AWG (0.000986" OD) (0.02505 mm OD) twisted pair wire. As shown in FIGS. 4 and 5, the electrical connection between leads $76_1$, $76_2$ of coil 74 and leads $63_1$, $63_2$ of conductor 62 is facilitated by conductive elements 90. Conductive elements 90 may be made from conductive materials such as copper and may have a surface finish such as electroless nickel/gold, silver, etc. Conductive elements 90 may also comprise a flex pad or flexible circuit affixed to one or more of the projections $84_1$, $84_2$. Leads $76_1$, $76_2$ of coil 74 and leads $63_1$, $63_2$ of conductor 62 are both electrically connected to conductive elements 90 to conduct the voltage induced in position sensor 26 to a proximal end of medical device 12.

Figure 5A:
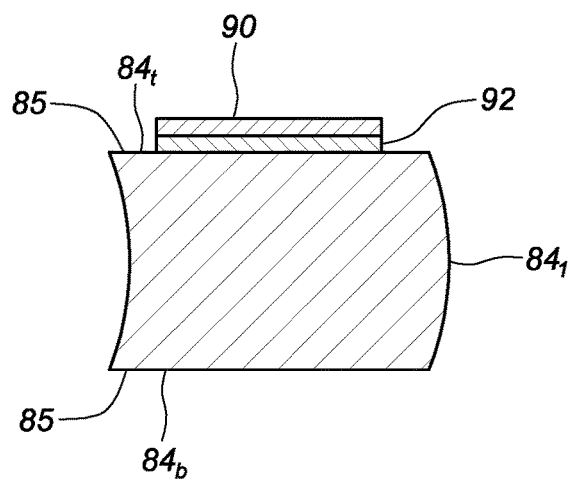
FIG. 5A is a cross-sectional view of a portion of the magnetic position sensor illustrated in FIG. 5 taken along line 5A-5A.

With reference to FIG. 5A, because various embodiments of core 80 are comprised of an electrically-conductive material, an insulating layer 92 may be located between projections $84_1$, $84_2$ and conductive elements 90, wherein insulating layer 92 is affixed to projections $84_1$, $84_2$ and conductive elements 90 are affixed to insulating layer 92. Insulating layer 92 may comprise any insulative material such as a thin film of insulating material, including but not limited to, a plastic material selected from the group comprising polyimide, polyetheretherketone (PEEK), polyester, polyethylene terephthalate (PET), and/or polyethylene naphthalate (PEN), such as those sold under the trademarks Tetoron®, Teonex®, and Melinex® and generally available from DuPont Tejin Films or a combination thereof, or polymers known by the trade name Parylene. However, in various embodiments, it will be understood that insulating layer 92 may comprise a coating of insulating material deposited, sprayed, or otherwise formed on core 80, such as, for example, an oxide coating, including, but not limited to, magnesium oxide, aluminum oxide, or any ceramic oxide as known in the art. In various embodiments, as is known in the art, the same or similar insulating layer may also be present between body 82 of core 80 and coil 74 to prevent shorting between core 80 and coil 74. In other embodiments, conductive wire 76 of coil 74 may be insulated negating the need for an insulating layer to be present on body 82 of core 80.

Coil 74 and conductor 62 may be coupled to conductive elements 90 by soldering leads $76_1$, $76_2$ of coil 74 and leads $63_1$, $63_2$ of conductor 62 to conductive elements 90. In such an embodiment, reflowed solder paste may be applied to conductive elements 90. Types of reflowed solder paste may include type 3 to 6 non-Pb solder pastes, such as Kester 520A SAC305. In accordance with another embodiment, conductive epoxy adhesives, such as Ablebond 2000, may be used to couple leads $76_1$, $76_2$ of coil 74 and leads $63_1$, $63_2$ of conductor 62 to conductive elements 90. Solder paste or conductive adhesive may be manually dispensed using a syringe, or it can be dispensed from automated equipment. After the paste or adhesive is applied, leads $76_1$, $76_2$ of coil 74 and leads $63_1$, $63_2$ of conductor 62 may be positioned such that leads $76_1$, $76_2$ of coil 74 and leads $63_1$, $63_2$ of conductor 62 contact the solder paste. Thereafter, position sensor 26 may then be placed in a curing oven or reflow oven to cure the adhesive and/or reflowed solder paste. This and other methods of electrically connecting leads $76_1$, $76_2$ of coil 74 with leads $63_1$, $63_2$ of conductor 62 are as discussed in greater detail in commonly owned PCT Publication No. WO 2015/16562 filed Jan. 27, 2015 (hereinafter the '562 application), the entire content of which is hereby incorporated herein by reference in its entirety for all purposes and as though fully set forth herein.

As can be seen FIGS. 3, 4, 5 and 5A, projections $84_1$, $84_2$ are substantially rectangularly shaped in cross-section and provide landing areas 85, which may be substantially flat or substantially smooth, on the top and bottom sides $84t$, $84b$ of projections $84_1$, $84_2$ for an electrical connection between coil 74 and conductor 62 to be made. The outer or peripheral sides of projections $84_1$, $84_2$ may follow the curvature of body 82 of core 80. Additionally, the internal sides of projections $84_1$, $84_2$ may follow the curvature of lumen 86. Thus, projections $84_1$, $84_2$ provide a location for an electrical connection. Because projections $84_1$, $84_2$ are integrally formed as a part of core 80 and are rigidly fixed with respect to body 82, projections $84_1$, $84_2$ provide locations to terminate leads $76_1$, $76_2$ of coil 74 that do not move relative to body 82 of core 80. Therefore, the landing areas 85 are adapted and arranged for electrical connection to leads $76_1$, $76_2$ of coil 74. The flat landing area 85 of projections $84_1$, $84_2$ provides increased mechanical and electrical integrity and reliability of position sensor 26 as compared to prior art position sensors with unsupported soldered electrical connections. The unsupported electrical connections of prior art position sensors tend to move in relation to the coil and over time, this movement causes breakage of the electrical connection rendering the position sensor unusable. While projections $84_1$, $84_2$ are shown as substantially rectangular in shape in cross-section, it will be understood that in other embodiments as described below, the core may include various different geometries of projections having landing areas without departing from the scope of the disclosure. Although landing areas 85 are shown as located on the top and bottom sides $84t$, $84b$ of projections $84_1$, $84_2$, it will be understood that in other embodiments landing areas 85 may be located on any side of projections $84_1$, $84_2$. For example, and without limitation, landing areas 85 may be located on the inner sides of projections $84_1$, $84_2$ proximate lumen 86. In other embodiments (for example and without limitation), landing areas 85 may be located on the outer radial sides of projections $84_1$, $84_2$.

In addition to providing a landing area 85 for leads $76_1$, $76_2$ of coil 74, projections $84_1$, $84_2$ of core 80 serve to increase the magnetic flux passing through coil 74 of position sensor 26. Projections $84_1$, $84_2$ are configured to generate magnetic flux lines that pass through position sensor 26 when subject to a magnetic field, thereby bringing a larger amount of the magnetic field into contact with position sensor 26 than would otherwise contact position sensor 26 without the presence of projections $84_1$, $84_2$. In various embodiments (for example and without limitation), projections $84_1$, $84_2$ may increase the induced voltage in coil 74 by about 60 percent over a core having no projections $84_1$, $84_2$. Depending on the geometry of projections $84_1$, $84_2$, in various embodiments, the increase in the induced voltage in coil 74 may be less than about 60 percent over a core having no projections $84_1$, $84_2$, while in other embodiments, the increase in the induced voltage in coil 74 may be more than about 60 percent over a core having no projections $84_1$, $84_2$.

Figure 6:
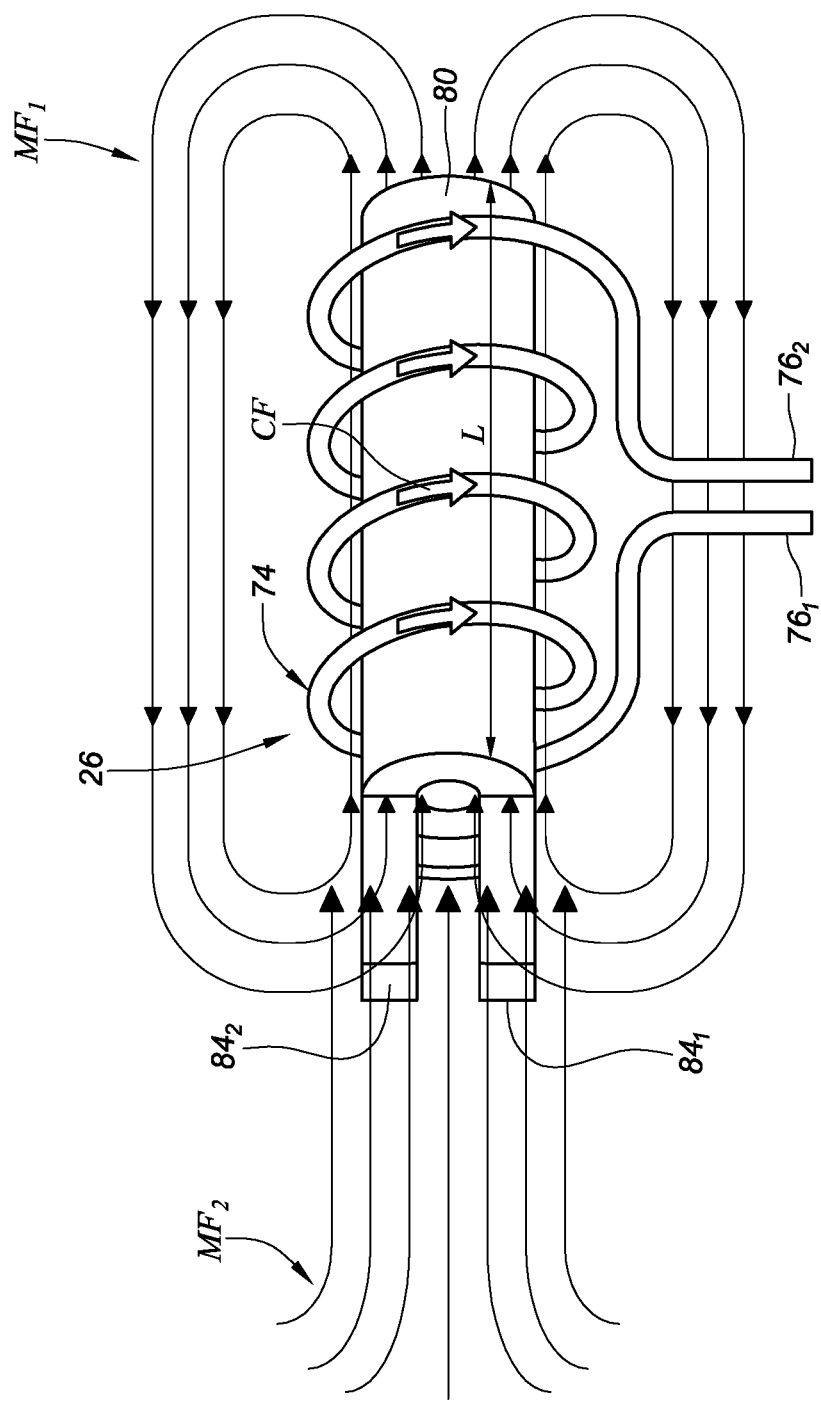
FIG. 6 is a schematic diagram of the magnetic position sensor illustrated in FIGS. 4 and 5 illustrating the presence of magnetic flux lines and induced current flow.

FIG. 6 is a schematic diagram of magnetic position sensor 26 having core 80 with projections $84_1$, $84_2$ extending therefrom illustrating the presence of magnetic flux lines $MF_1$ and $MF_2$, and induced current flow CF. As a result of being placed in a magnetic field, such as magnetic field $F_M$ of FIG. 1, magnetic flux lines $MF_1$ are formed by coil 74, which induces a voltage in coil 74.

The below constitutive equation (Equation (1)) describes the voltage V induced in a typical position sensor having a core, wherein the core does not include any projections as described herein. The below equation provides a starting point for determining the induced voltages in the types of position sensors having projections as described herein. The voltage V induced in coil windings between lead wires of a typical position sensor is defined in Equation (1) below, where μ=magnetic permeability (core material), N=total number of turns, A=cross-sectional area of core (L=length of core), and B=magnetic field strength (output of drive coil, in P-P or RMS).

$$V = 2\pi \mu NABf \qquad \text{Equation (1)}$$

As can be seen from Equation (1), the induced voltage V is increased if the magnetic permeability μ increases or if the area A increases. It is, however, undesirable to increase the area A of the core due to space limitations within medical device 12, as well as the overall outer diameter size limitations of medical device 12. It is also not always possible to simply increase the number of turns N of the coil without unduly affecting the flexibility of the catheter. For example, adding windings in the axial length makes the sensor longer, while adding winding in the radial direction makes the sensor thicker, both of which may make the catheter undesirably stiffer.

As a result of being subject to the same magnetic field that position sensor 26 is subject to, magnetic flux lines $MF_2$ are formed by projections $84_1$, $84_2$. Some of magnetic flux lines $MF_2$ pass through position sensor 26. With reference to Equation (1), projections $84_1$, $84_2$ can be viewed as increasing the permeability μ of the core, increasing the length L of the core, or as increasing the magnetic field strength B impacting the core. As a result of the inclusion of projections $84_1$, $84_2$ extending from body 82 of core 80, various design parameters of position sensor 26, such as voltage V or area A, can be changed. For example, the size $$\left( \text{e.g., diameter } D, \text{ wherein} = \pi \left( \frac{D}{2} \right)^2 \right)$$

of coil windings 76 could be reduced without reducing the signal strength or V by using appropriately sized projections $84_1$, $84_2$. Thus, increasing the length of projections $84_1$, $84_2$ increases the magnetic flux passing through position sensor 26. Therefore, projections $84_1$, $84_2$ function similar to the high magnetic permeability antennas described in co-pending PCT Application No. PCT/US16/22669 and U.S. patent application Ser. No. 15/072,185, both filed on Mar. 16, 2016, and both to Buesseler et al. the entire contents of which are incorporated herein by reference in their entirety for all purposes and as though fully set forth herein.

Figure 7:
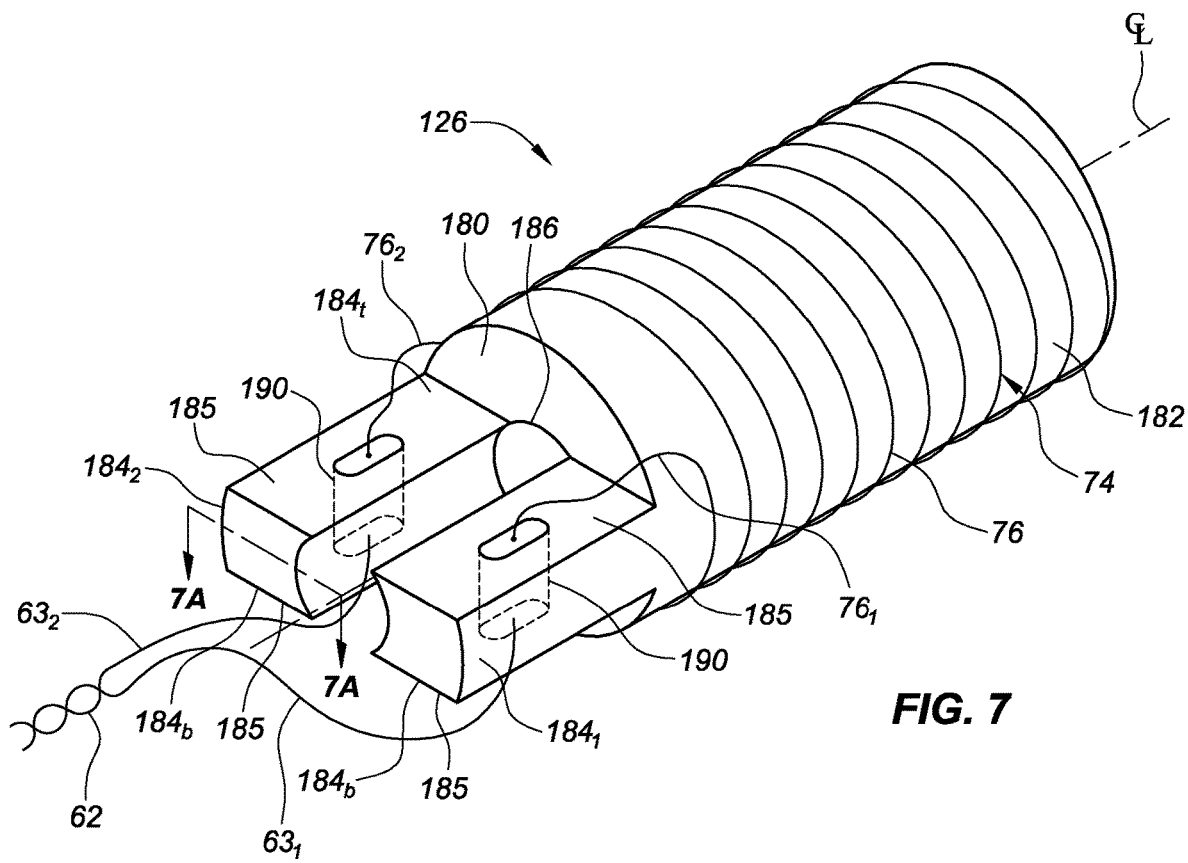
FIG. 7 is an isometric view of a magnetic position sensor according to another embodiment of the disclosure.
Figure 7A:
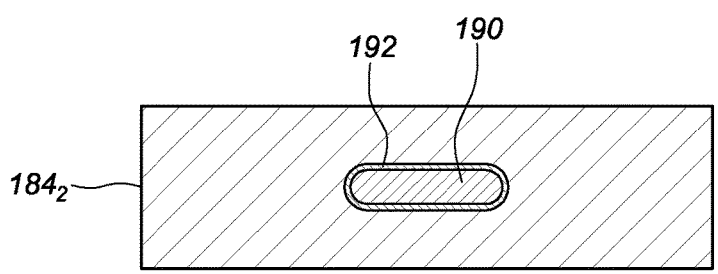
FIG. 7A is a cross-sectional view of a portion of the magnetic position sensor illustrated in FIG. 7 taken along line 7A-7A.

Another embodiment of a position sensor 126 of the disclosure is illustrated in FIGS. 7 and 7A and is described below. Some features of one or more of position sensors 26 and 126 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

FIG. 7 is an isometric view of magnetic position sensor 126 having core 180 and coil 74. In the embodiment shown, core 180 comprises a body 182 from which one or more projections $184_1$, $184_2$ extend therefrom. In various embodiments, core 180 comprises a annular core constructed of high permeability material. Thus, core 180 may include lumen 186 extending through the axial length of core 180. Projections $184_1$, $184_2$ are integrally formed as a part of core 180 and are rigidly fixed with respect to body 182 of core 180. Accordingly, any movement between projections $184_1$, $184_2$ and body 182 is reduced or eliminated. Projections $184_1$, $184_2$ provide landing areas 185 which are adapted and arranged for electrical connection to leads $76_1$, $76_2$ of coil 74 described below. The flat landing area 185 of projections $184_1$, $184_2$ provides increased mechanical and electrical integrity and reliability of position sensor 126 as compared to prior art position sensors with unsupported soldered electrical connections.

Position sensor 126, further comprises coil 74 surrounding core 180. Coil 74 of position sensor 126 may be formed from a length of conductive wire 76, such as copper, spirally wound about center line $C_L$ of core 180. Coil 74 generally only surrounds body 182 of core 180 with projections 182 not being surrounded by coil 74. Leads $76_1$, $76_2$ of coil 74 terminate on projections $184_1$, $184_2$ where leads $76_1$, $76_2$ make an electrical connection with leads $63_1$, $63_2$ of conductor 62. As shown in FIGS. 7 and 7A, the electrical connection between leads $76_1$, $76_2$ and leads $63_1$, $63_2$ of conductor 62 is facilitated by conductive paths 190 extending from the top sides 184t of projections $184_1$, $184_2$ to the bottom sides 184b of projections $184_1$, $184_2$.

One of ordinary skill in the art will understand that conductive paths 190 can be formed by (for example and without limitation) constructing through vias and/or blind vias through projections $184_1$, $184_2$ from a first side to a second side of projections $184_1$, $184_2$. In one embodiment, conductive paths 190 are formed by creating through vias between top side and bottom sides 184t, 184b of projections 184, lining the through vias with an insulating material or layer 192 such as the insulating materials or layers described in greater detail elsewhere herein, and filling the through vias with a conductive material, such as copper. In another embodiment, conductive paths 190 are formed by laser-drilling through projections $184_1$, $184_2$ and, thereafter, lining the through vias with an insulating material or layer 192 and filling the drilled holes with conductive paste. Leads $76_1$, $76_2$ of coil 74 and/or leads $63_1$, $63_2$ of conductor 62 may be electrically connected to conductive paths 190 during the curing of the conductive paste. Thus, leads $76_1$, $76_2$ of coil 74 and leads $63_1$, $63_2$ of conductor 62 are both electrically connected to conductive paths 190 to conduct the voltage induced in position sensor 126 to proximal end of medical device 12. As shown, for example, leads $76_1$, $76_2$ of coil 74 are electrically connected to conductive paths 190 proximate the top side 184t of projections $184_1$, $184_2$ and leads $63_1$, $63_2$ of conductor 62 are electrically connected to conductive paths 190 proximate the bottom side 184b of projections $184_1$, $184_2$. In various embodiments, as is known in the art, the same or similar insulating layer may also be present between body 182 of core 180 and coil 74 to prevent shorting between core 180 and coil 74. In other embodiments, conductive wire 76 of coil 74 may be insulated negating the need for an insulating layer to be present on body 182 of core 180. In various embodiments, core 180 may be made of a non-conductive material, thus the insulating layer 192 would not be required.

Figure 8:
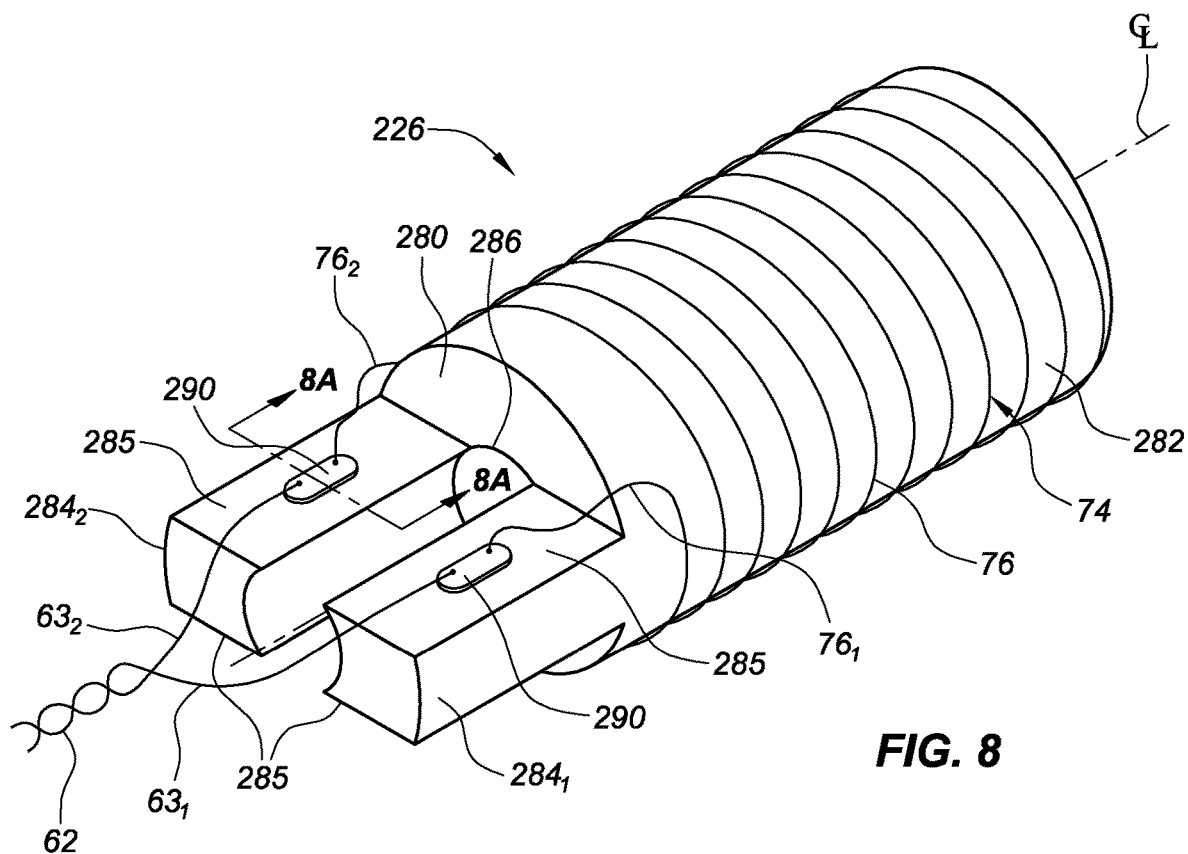
FIG. 8 is an isometric view of a magnetic position sensor according to another embodiment of the disclosure.
Figure 8A:
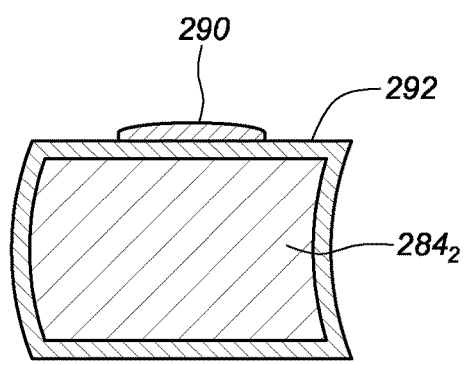
FIG. 8A is a cross-sectional view of a portion of the magnetic position sensor illustrated in FIG. 8 taken along line 8A-8A.

Another embodiment of a position sensor 226 of the disclosure is illustrated in FIGS. 8 and 8A and is described below. Some features of one or more of position sensors 26, 126, and 226 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

FIG. 8 is an isometric view of magnetic position sensor 226 having core 280 and coil 74. In the embodiment shown, core 280 comprises a body 282 from which one or more projections $284_1$, $284_2$ extend therefrom. In various embodiments, core 280 comprises a annular core constructed of high permeability material. Thus, core 280 may include lumen 286 extending through the axial length of core 280. Projections $284_1$, $284_2$ are integrally formed as a part of core 280 and are rigidly fixed with respect to body 282 of core 280. Accordingly, any movement between projections $284_1$, $284_2$ and body 282 is reduced or eliminated. Projections $284_1$, $284_2$ provide landing areas 285 which are adapted and arranged for electrical connection to leads $76_1$, $76_2$ of coil 74 described below. The flat landing area 285 of projections $284_1$, $284_2$ provides increased mechanical and electrical integrity and reliability of position sensor 226 as compared to prior art position sensors with unsupported soldered electrical connections.

Position sensor 226, further comprises coil 74 surrounding core 280. Coil 74 of position sensor 226 may be formed from a length of conductive wire 76, such as copper, spirally wound about center line $C_L$ of core 280. Coil 74 generally only surrounds body 282 of core 280 with projections $284_1$, $284_2$ not being surrounded by coil 74. Leads $76_1$, $76_2$ of coil 74 terminate on projections $284_1$, $284_2$ where leads $76_1$, $76_2$ of coil 74 make an electrical connection with leads $63_1$, $63_2$ of conductor 62. As shown in FIGS. 8 and 8A, the electrical connection between leads $76_1$, $76_2$ and conductor 62 is facilitated by conductive elements 290 on one or more of projections $284_1$, $284_2$. That is, leads $76_1$, $76_2$ of coil 74 and leads $63_1$, $63_2$ of conductor 62 are both electrically connected to conductive elements 290 to conduct the voltage induced in position sensor 226 to proximal end of medical device 12. With reference to FIG. 8A, because various embodiments of core 280 are comprised of an electrically conductive material, core 280 may be coated with an insulating material forming an insulating layer 292 over core 280. Conductive elements 290 are located on top of insulating layer 292, with insulating layer 292 between projections $284_1$, $284_2$ and conductive elements 290. In various embodiments, as is known in the art, the same or similar insulating layer may also be present between body 282 of core 280 and coil 74 to prevent shorting between core 280 and coil 74. In other embodiments, conductive wire 76 of coil 74 may be insulated negating the need for an insulating layer to be present on body 282 of core 280. In various embodiments, core 280 may be made of a non-conductive material, thus the insulating layer 292 would not be required.

Conductive elements 290 may be made from conductive materials such as copper and may have a surface finish such as electroless nickel/gold, silver, etc. In other embodiments, it will be understood that conductive elements 290 may be formed of a conductive paste or epoxy. Leads $76_1$, $76_2$ of coil 74 and leads $63_1$, $63_2$ of conductor 62 may be positioned on projections $284_1$, $284_2$ and solder paste or conductive epoxy may be deposited over leads $76_1$, $76_2$ of coil 74 and leads $63_1$, $63_2$ of conductor 62 and the solder paste or conductive epoxy is allowed to cure, forming the electrical connection between leads $76_1$, $76_2$ of coil 74 and leads $63_1$, $63_2$ of conductor 62. Alternatively, a solder paste or conductive epoxy may be deposited over projections $284_1$, $284_2$ and leads $76_1$, $76_2$ of coil 74 and leads $63_1$, $63_2$ of conductor 62 may be inserted into the solder paste or conductive epoxy, which is then allowed to cure, forming the electrical connection between leads $76_1$, $76_2$ of coil 74 and leads $63_1$, $63_2$ of conductor 62.

Figure 9:
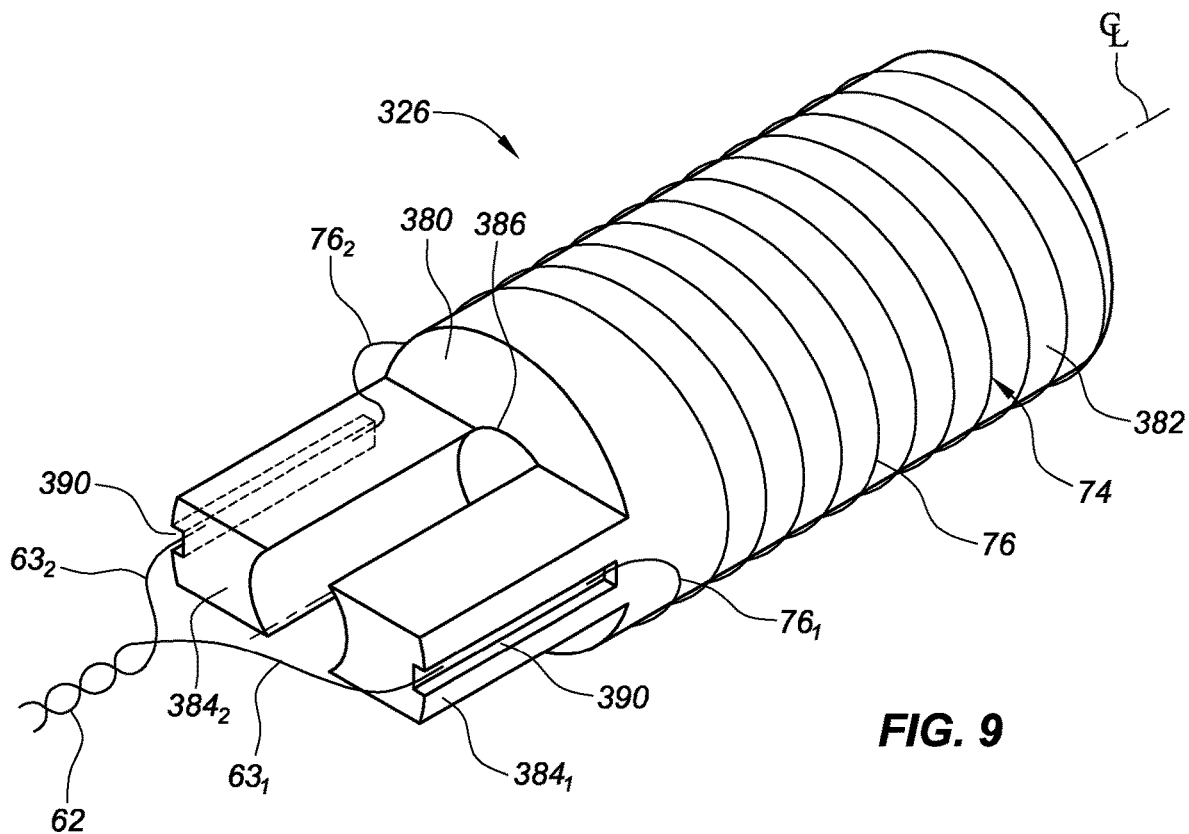
FIG. 9 is an isometric view of a magnetic position sensor according to another embodiment of the disclosure.
Figure 9A:
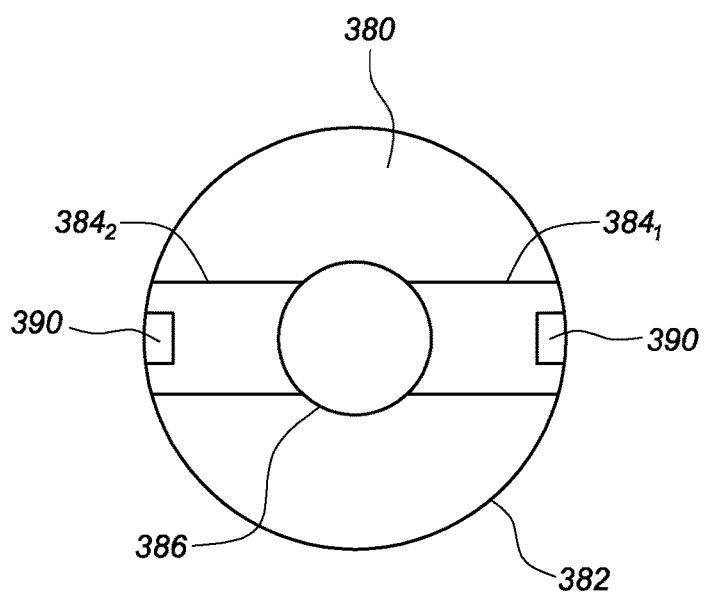
FIG. 9A is a view of the left end (as oriented in FIG. 9) of a portion of the magnetic position sensor illustrated in FIG. 9.

Another embodiment of a position sensor 326 of the disclosure is illustrated in FIGS. 9 and 9A and is described below. Some features of one or more of position sensors 26, 126, 226, and 326 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

FIG. 9 is an isometric view of magnetic position sensor 326 having core 380 and coil 74. In the embodiment shown, core 380 comprises a body 382 from which one or more projections $384_1$, $384_2$ extend therefrom. Core 380 comprises a annular core constructed of high permeability material. Thus, core 380 may include lumen 386 extending through the axial length of core 380. Projections $384_1$, $384_2$ are integrally formed as a part of core 380 and are rigidly fixed with respect to body 382 of core 380. Accordingly, any movement between projections $384_1$, $384_2$ and body 382 is reduced or eliminated. As shown in FIGS. 9 and 9A, projections $384_1$, $384_2$ further include a groove or channel 390 along the outside length of projections $384_1$, $384_2$. Grooves or channels 390 provide a location for the electrical connection of coil 74 and conductor 62 along the outside of core 380 while not increasing the diameter of magnetic position sensor 326 in the location of projections 384. This allows for an alternate electrical connection location without needing to reduce the diameter of core 280.

Position sensor 326, further comprises coil 74 surrounding core 380. Coil 74 of position sensor 326 may be formed from a length of conductive wire 76, such as copper, spirally wound about center line $C_L$ of core 380. Coil 74 generally only surrounds body 382 of core 380 with projections 382 not being surrounded by coil 74. Leads $76_1$, $76_2$ of coil 74 terminate in grooves 390 on projections $284_1$, $284_2$ where leads $76_1$, $76_2$ of coil 74 make an electrical connection with leads $63_1$, $63_2$ of conductor 62. As shown in FIGS. 9 and 9A, the electrical connection between leads $76_1$, $76_2$ and conductor 62 is facilitated by conductive areas (not shown) located in the grooves 390 on one or more of projections $184_1$, $184_2$. That is, leads $76_1$, $76_2$ of coil 74 and leads $63_1$, $63_2$ of conductor 62 are both electrically connected to the conductive areas to conduct the voltage induced in position sensor 226 to proximal end of medical device 12. The electrical connection of leads $76_1$, $76_2$ of coil 74 and leads $63_1$, $63_2$ of conductor 62 within grooves 390 may be accomplished in a variety of ways, including, but not limited to, flex pads, flex circuits, conductive elements or areas, solder paste, and/or conductive epoxy as described in greater detail elsewhere herein with respect to other embodiments.

Although grooves 390 are shown as located on the outer radial sides of projections $384_1$, $384_2$, it will be understood that in other embodiments grooves 390 may be located on any side of projections $384_1$, $384_2$. For example, and without limitation, grooves 390 may be located on the inner sides of projections $384_1$, $384_2$ proximate lumen 386. In other embodiments (for example and without limitation), grooves 390 may be located on the tops and/or bottoms of projections $384_1$, $384_2$. Additionally, while one groove 390 is shown on each projection $384_1$, $384_2$, it will be understood that in yet other embodiments (for example and without limitation), that two grooves may be located on a single projection $384_1$ or $384_2$. Accordingly, the electrical connection between leads $76_1$, $76_2$ of coil 74 and leads $63_1$, $63_2$ of conductor 62 may be made on one projection $384_1$ or $384_2$ instead of both projections $384_1$, $384_2$.

Figure 10:
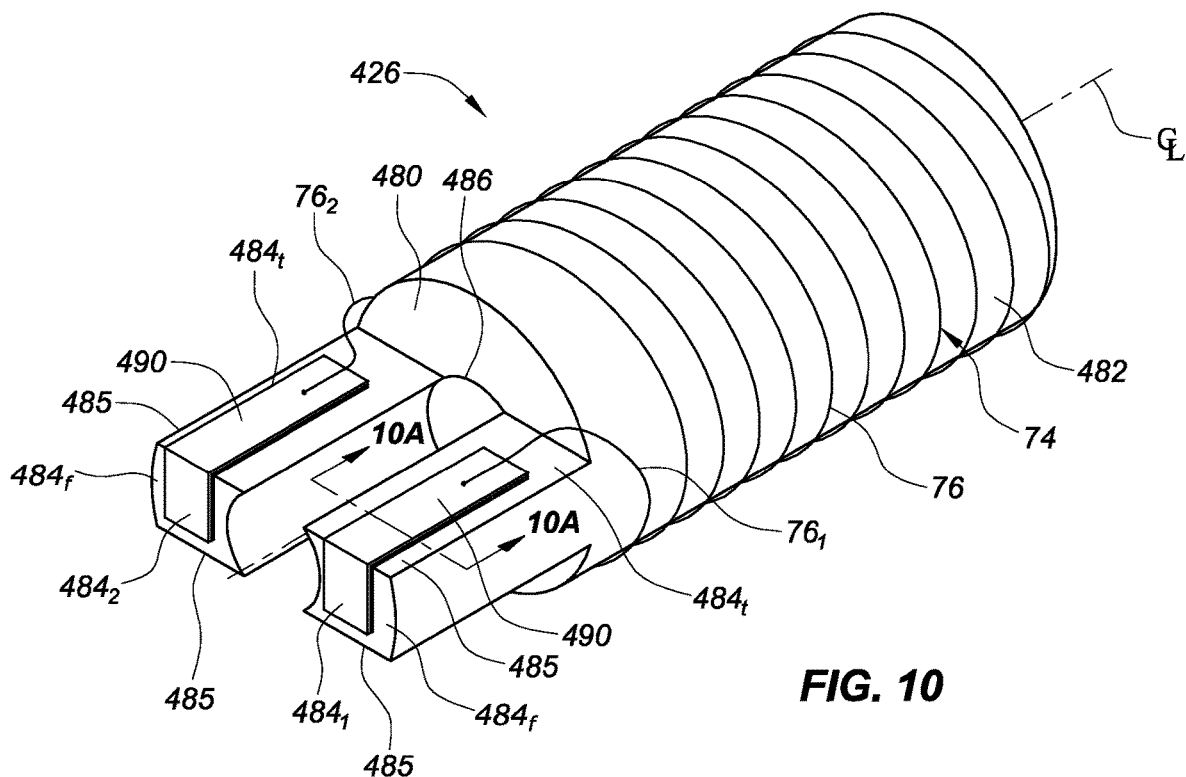
FIG. 10 is an isometric view of a magnetic position sensor according to another embodiment of the disclosure.
Figure 10A:
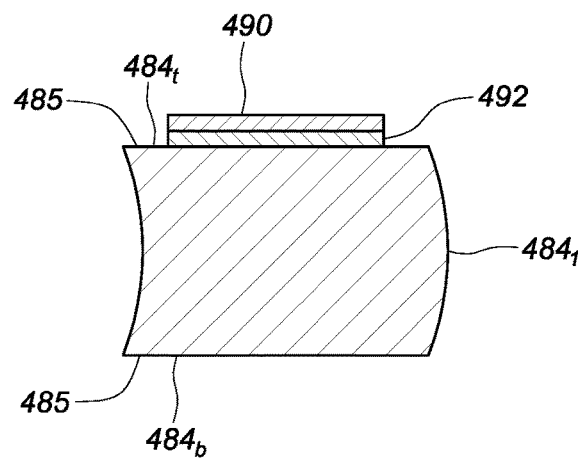
FIG. 10A is a cross-sectional view of a portion of the magnetic position sensor illustrated in FIG. 10 taken along line 10A-10A.
Figure 11:
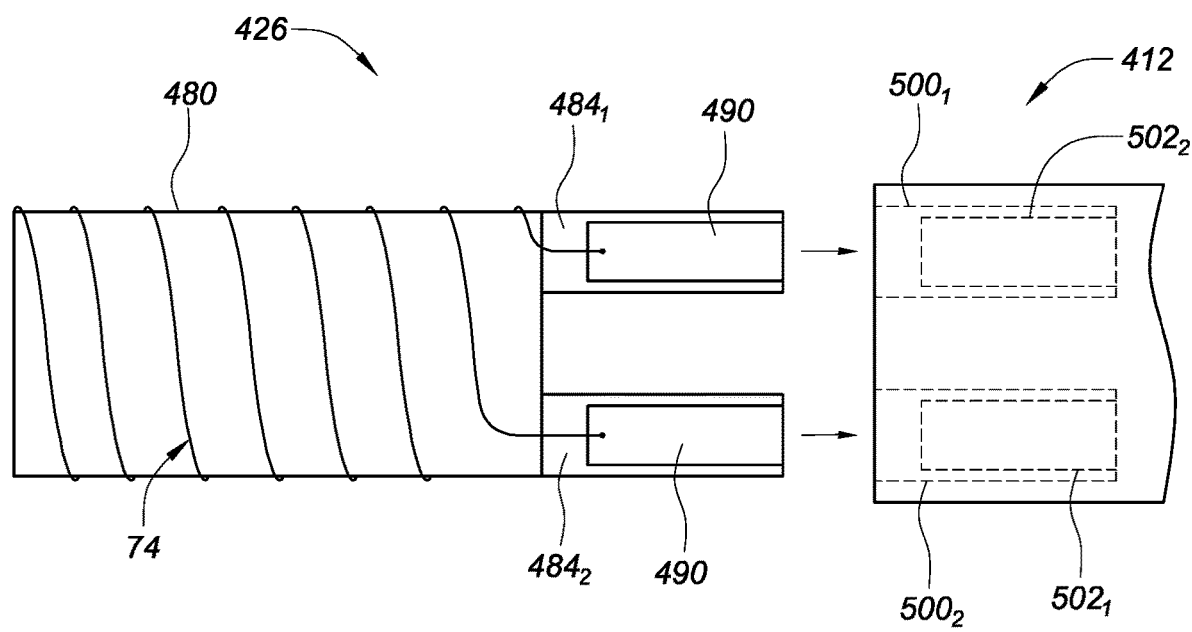
FIG. 11 is a top view of a magnetic position sensor having a plug-in connection with a medical device according to one embodiment of the disclosure.

Another embodiment of a position sensor 426 of the disclosure is illustrated in FIGS. 10, 10A, and 11 and is described below. Some features of one or more of position sensors 26, 126, 226, 326, and 426 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

FIG. 10 is an isometric view of magnetic position sensor 426 having core 480 and coil 74. In the embodiment shown, core 480 comprises a body 482 from which one or more projections $484_1$, $484_2$ extend therefrom. Core 480 comprises a annular core constructed of high permeability material. Thus, core 480 may include lumen 486 extending through the axial length of core 480. Projections $484_1$, $484_2$ are integrally formed as a part of core 480 and are rigidly fixed with respect to body 482 of core 480. Accordingly, any movement between projections $484_1$, $484_2$ and body 482 is reduced or eliminated. Projections $484_1$, $484_2$ provide landing areas 485 which are adapted and arranged for electrical connection to leads $76_1$, $76_2$ of coil 74 described below. The flat landing area 485 of projections $484_1$, $484_2$ provide increased mechanical and electrical integrity and reliability of position sensor 426 as compared to prior art position sensors with unsupported soldered electrical connections.

Position sensor 426, further comprises coil 74 surrounding core 480. Coil 74 of position sensor 426 may be formed from a length of conductive wire 76, such as copper, spirally wound about center line $C_L$ of core 480. Coil 74 generally only surrounds body 482 of core 480 with projections $484_1$, $484_2$ not being surrounded by coil 74. Leads $76_1$, $76_2$ of coil 74 terminate on projections $484_1$, $484_2$ where leads $76_1$, $76_2$ are electrically connected with conductive elements 490. As shown, conductive elements 490 may be located along the top sides 484t of projections $484_1$, $484_2$ and may optionally extend downward along front sides 484f of projections $484_1$, $484_2$.

Because core 480 may be comprised of an electrically conductive material, an insulating layer 492 (see FIG. 10A) may be located between projections $484_1$, $484_2$ and conductive elements 490 to prevent shorting between core 480 and conductive elements 490. Insulating layer 492 is affixed to projections $484_1$, $484_2$ and conductive elements 490 are affixed to insulating layer 492. Insulating layer 492 may comprise any insulative material such as a thin film of insulating material, including but not limited to, a plastic material selected from the group comprising polyimide, polyetheretherketone (PEEK), polyester, polyethylene terephthalate (PET), and/or polyethylene naphthalate (PEN), such as those sold under the trademarks Tetoron®, Teonex®, and Melinex® and generally available from DuPont Tejin Films or a combination thereof, or polymers known by the trade name Parylene. However, in various embodiments, it will be understood that insulating layer 492 may comprise a coating of insulating material deposited, sprayed or otherwise formed on core 480 such as, for example, an oxide coating, including, but not limited to, magnesium oxide, aluminum oxide, or any ceramic oxide as known in the art. In various embodiments, as is known in the art, the same or similar insulating layer may also be present between body 482 of core 480 and coil 74 to prevent shorting between core 480 and coil 74. In other embodiments, conductive wire 76 of coil 74 may be insulated negating the need for an insulating layer to be present on body 482 of core 480. In various embodiments, core 480 may be made of a non-conductive material, thus the insulating layer 492 would not be required.

Now with reference to FIG. 11, position sensor 426 may be plugged into a medical device 412, such as for example and without limitation, a catheter, guidewire, or introducer. Medical device 412 includes receptacles $500_1$, $500_2$ which may correspond in size and geometry to projections $484_1$, $484_2$. Housed within receptacles $500_1$, $500_2$ are conductive elements $502_1$, $502_2$ that are electrically connected to conductor 62. Conductive elements $502_1$, $502_2$ in medical device 412 make physical and electrical contact with conductive elements 490 when position sensor 426 is plugged into receptacles $500_1$, $500_2$ of medical device 412. This plug-in electrical connection eliminates the need to solder leads of conductor 62 to conductive elements 490 of position sensor 426. Moreover, the plug-in connection allows easy assembly of position sensor 426 into medical device 412, as well as, easy replacement of a new position sensor 426 into medical device 412 by an end user should the need or desire to replace position sensor 426 arise. In various embodiments (for example only and without limitation), the receptacles $500_1$, $500_2$ in medical device 412 may be low insertion force (LIF) sockets or zero insertion force (ZIF) sockets as is known in the art.

Figure 12:
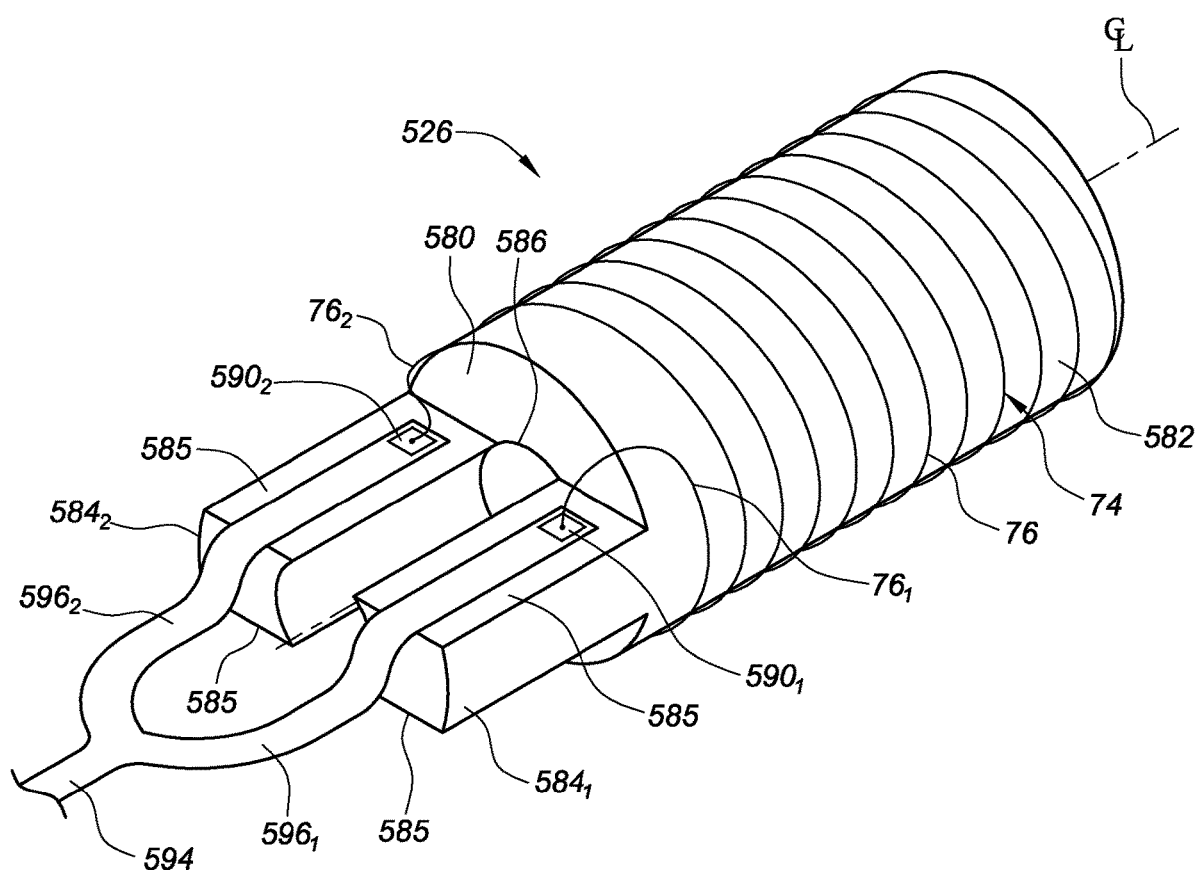
FIG. 12 is an isometric view of a magnetic position sensor according to another embodiment of the disclosure.

Another embodiment of a position sensor 526 of the disclosure is illustrated in FIG. 12 and is described below. Some features of one or more of position sensors 26, 126, 226, 326, 426, and 526 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

FIG. 12 is an isometric view of magnetic position sensor 526 having core 580 and coil 74. In the embodiment shown, core 580 comprises a body 582 from which one or more projections $584_1$, $584_2$ extend therefrom. Core 580 comprises a annular core constructed of high permeability material. Thus, core 580 may include lumen 586 extending through the axial length of core 580. Projections $584_1$, $584_2$ are integrally formed as a part of core 580 and are rigidly fixed with respect to body 582 of core 580. Accordingly, any movement between projections $584_1$, $584_2$ and body 582 is reduced or eliminated. Projections $584_1$, $584_2$ provide landing areas 585 which are adapted and arranged for electrical connection to leads $76_1$, $76_2$ of coil 74 described below. The flat landing area 585 of projections 584$_1$, 584$_2$ provide increased mechanical and electrical integrity and reliability of position sensor 526 as compared to prior art position sensors with unsupported soldered electrical connections.

Position sensor 526, further comprises coil 74 surrounding core 580. Coil 74 of position sensor 526 may be formed from a length of conductive wire 76, such as copper, spirally wound about center line C$_L$ of core 580. Coil 74 generally only surrounds body 582 of core 580 with projections 584$_1$, 584$_2$ not being surrounded by coil 74. Leads 76$_1$, 76$_2$ of coil 74 terminate on projections 584$_1$, 584$_2$ where leads 76$_1$, 76$_2$ are electrically connected with conductive elements 590$_1$, 590$_2$ on a flexible printed circuit 594. Flexible printed circuit 594 may serve the same function as conductor wire 62 shown in various embodiments herein. As shown, flexible printed circuit 594 has a Y-shaped distal end having two legs 596$_1$, 596$_2$, with each leg having a conductive element 590$_1$, 590$_2$. Legs 596$_1$, 596$_2$ may be adhered or affixed to projections 584$_1$, 584$_2$ in a variety of ways as is known in the art, including, but not limited to adhesives, tapes, etc. Flexible printed circuit 594 has a proximal end (not shown) which may extend to proximal end of medical device 12 (shown in, for example, FIG. 1). Flexible printed circuit 594 may include the twisted pair conductors made using conductive ink such as those described in the aforementioned United States Publication No. 2015/0374254 to Sobe, the entire content of which is incorporated herein by reference in its entirety for all purposes and as though fully set forth herein. The electrical connection between leads 76$_1$, 76$_2$ of coil 74 and conductive elements 590$_1$, 590$_2$ on a flexible printed circuit 594 may be accomplished in a variety of ways known in the art and as described in greater detail elsewhere herein, including but not limited to, solder, solder paste, conductive adhesive.

Figure 13:
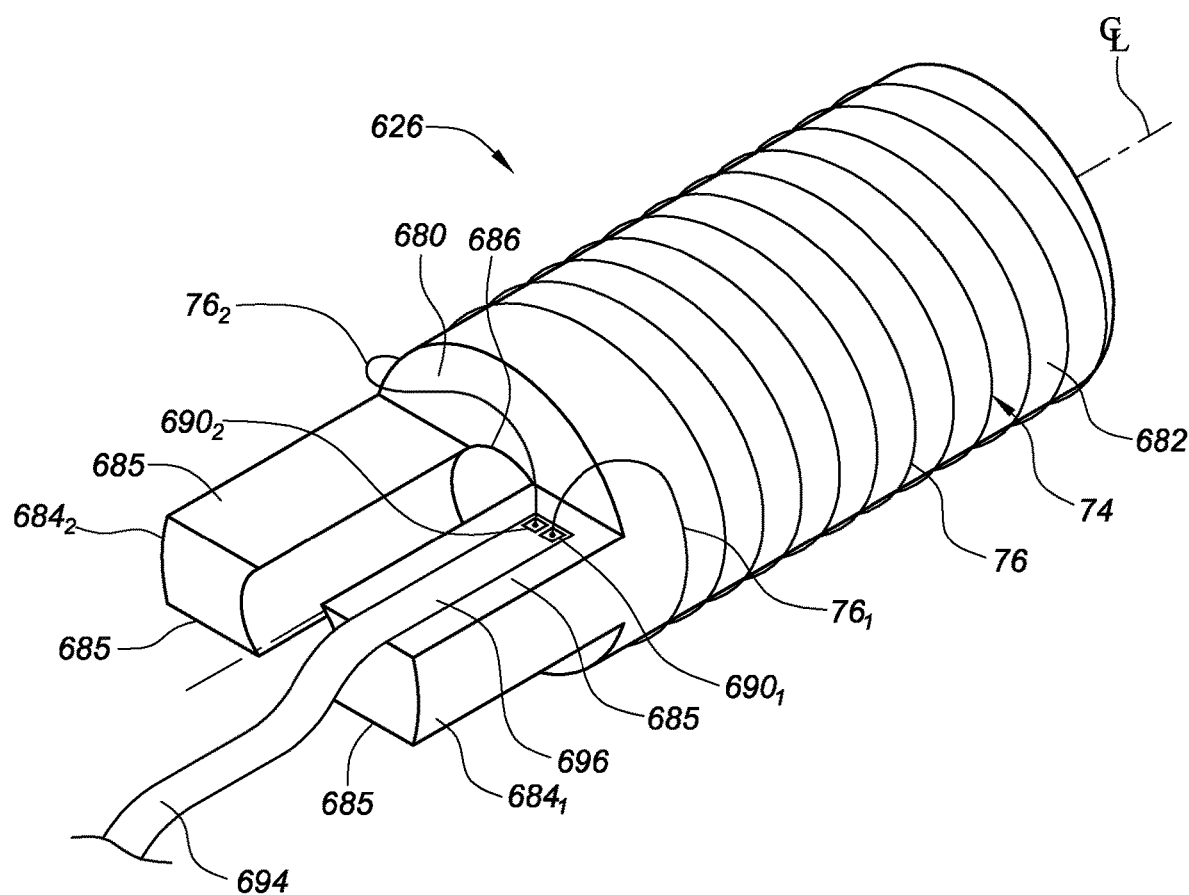
FIG. 13 is an isometric view of a magnetic position sensor according to another embodiment of the disclosure.

Another embodiment of a position sensor 626 of the disclosure is illustrated in FIG. 13 and is described below. Some features of one or more of position sensors 26, 126, 226, 326, 426, 526, and 626 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

FIG. 13 is an isometric view of magnetic position sensor 626 having core 680 and coil 74. In the embodiment shown, core 680 comprises a body 682 from which one or more projections 684$_1$, 684$_2$ extend therefrom. Core 680 comprises a annular core constructed of high permeability material. Thus, core 680 may include lumen 686 extending through the axial length of core 680. Projections 684$_1$, 684$_2$ are integrally formed as a part of core 680 and are rigidly fixed with respect to body 682 of core 680. Accordingly, any movement between projections 684$_1$, 684$_2$ and body 682 is reduced or eliminated. Projections 684$_1$, 684$_2$ provide landing areas 685 which are adapted and arranged for electrical connection to leads 76$_1$, 76$_2$ of coil 74 described below. The flat landing area 685 of projections 684$_1$, 684$_2$ provide increased mechanical and electrical integrity and reliability of position sensor 626 as compared to prior art position sensors with unsupported soldered electrical connections.

Position sensor 626 further comprises coil 74 surrounding core 680. Coil 74 of position sensor 626 may be formed from a length of conductive wire 76, such as copper, spirally wound about center line C$_L$ of core 680. Coil 74 generally only surrounds body 682 of core 680 with projections 684$_1$, 684$_2$ not being surrounded by coil 74. Leads 76$_1$, 76$_2$ of coil 74 terminate on projections 684$_1$, 684$_2$, respectively, where leads 76$_1$, 76$_2$ are electrically connected with conductive elements 690$_1$, 690$_2$, respectively, on a flexible printed circuit 694. Flexible printed circuit 694 may serve the same function as conductor wire 62 shown in various embodiments herein. As compared to flexible printed circuit 594 of FIG. 12, flexible printed circuit 694 has a single distal portion 696 having a pair of conductive elements 690$_1$, 690$_2$. Thus, unlike flexible printed circuit 594 of FIG. 12, leads 76$_1$, 76$_2$ of coil 74 connect to the single distal portion 696 of flexible printed circuit 694 with the single distal portion 696 having two conductive elements 690$_1$, 690$_2$, one for each lead 76$_1$, 76$_2$ of coil 74. Moreover, for example only and without limitation, flexible printed circuit 694 is affixed to only one projection 684$_1$. Distal portion 696 may be adhered or affixed to either one of projections 684$_1$, 684$_2$ in a variety of ways as is known in the art, including, but not limited to adhesives, tapes, etc. Flexible printed circuit 694 has a proximal end (not shown) which may extend to proximal end of medical device 12 (shown in, for example, FIG. 1). Flexible printed circuit 694 may include the twisted pair conductors made using conductive ink such as those described in the aforementioned U. S. Publication No. 2015/0374254 to Sobe, the entire content of which is incorporated herein by reference in its entirety for all purposes and as though fully set forth herein. The electrical connection between leads 76$_1$, 76$_2$ of coil 74 and conductive elements 690$_1$, 690$_2$ on a flexible printed circuit 694 may be accomplished in a variety of ways known in the art and as described in greater detail elsewhere herein, including but not limited to, solder, solder paste, conductive adhesive.

While various core designs having substantially elongate rectangular projections with alternative electrical connections have been shown herein, it will be understood that in other embodiments, the core may include various different geometries of projections having landing areas adapted and arranged for electrical connection to leads of a coil without departing from the scope of the disclosure. Now with reference to FIGS. 14-21, other embodiments of cores 780, 880, 980, 1080, 1180, 1280, 1380, 1480 for use in position sensors of the disclosure are illustrated described below. Some features of one or more of cores 80, 180, 280, 380, 480, 580, 680, 780, 880, 980, 1080, 1180, 1280, 1380, 1480 are common to one another and, accordingly, descriptions of such features in one embodiment should be understood to apply to other embodiments. Furthermore, particular characteristics and aspects of one embodiment may be used in combination with, or instead of, particular characteristics and aspects of another embodiment.

Figure 14:
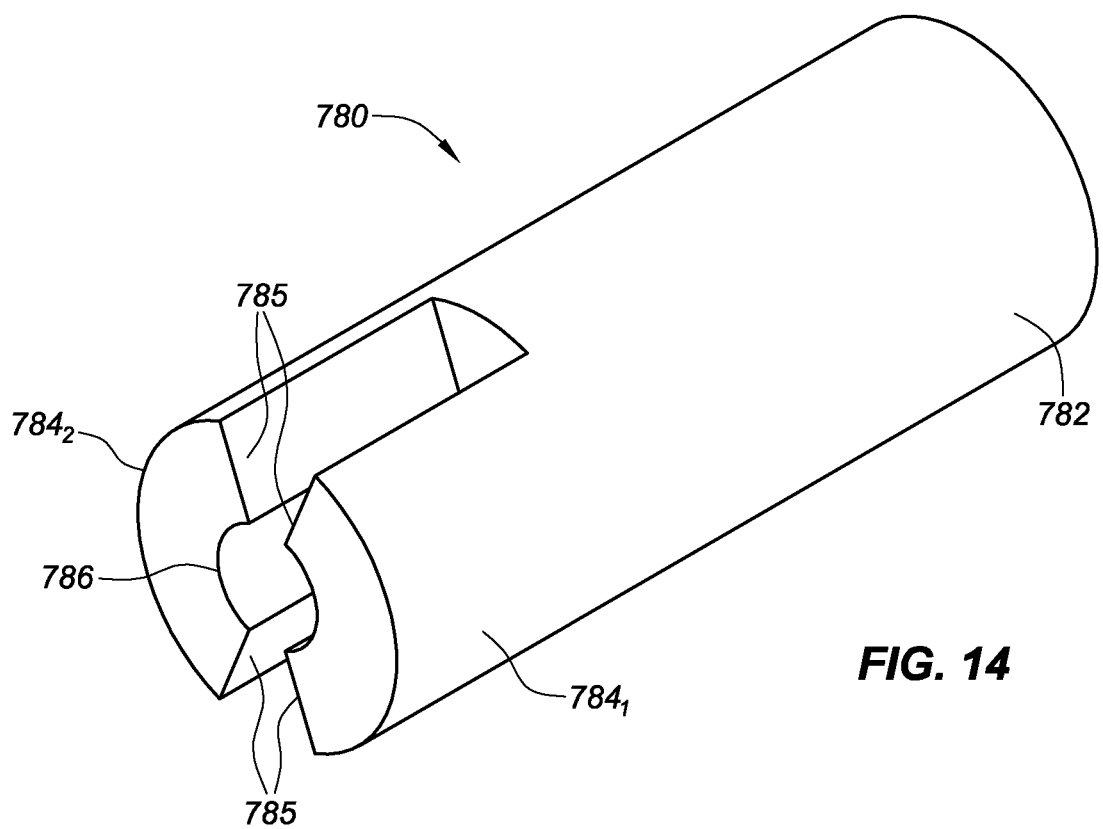
FIG. 14 is an isometric view of a core having a body and projections extending therefrom according to another embodiment of the disclosure.
Figure 14A:
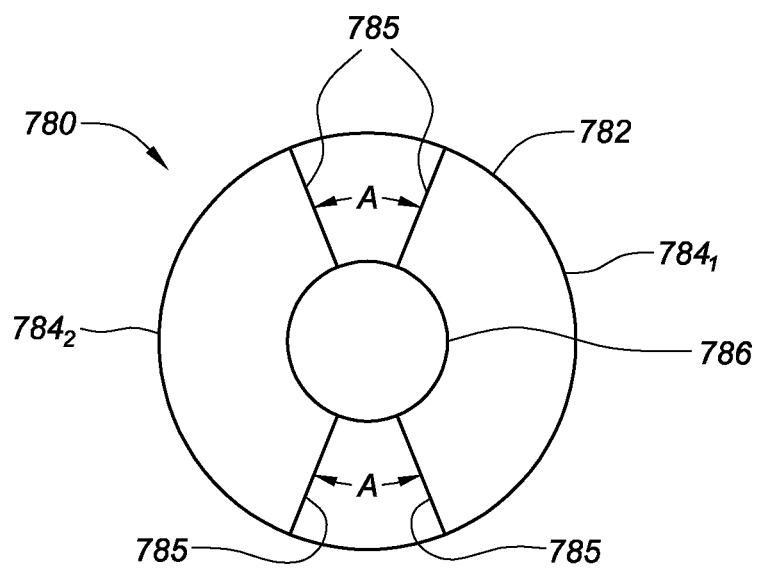
FIG. 14A is a view of the left end (as oriented in FIG. 14) of the core illustrated in FIG. 14.

FIGS. 14 and 14A show a core 780 comprising a body 782 from which one or more projections 784$_1$, 784$_2$ having a sector or pie-shaped cross-section extend therefrom. A lumen 786 is shown extending through core 780. As shown (for example only and without limitation), each sector or pie-shaped projection 784$_1$, 784$_2$ may sweep across an angle of about 120 degrees. Each projection provides two landing areas 785 at which an electrical connection between a coil and a conductor may be made as described in greater detail elsewhere herein. Due to the narrow areas A between sector or pie-shaped projections 784$_1$, 784$_2$, the landing areas 785, and any electrical connection located thereon, are protected from physical disruption.

Figure 15:
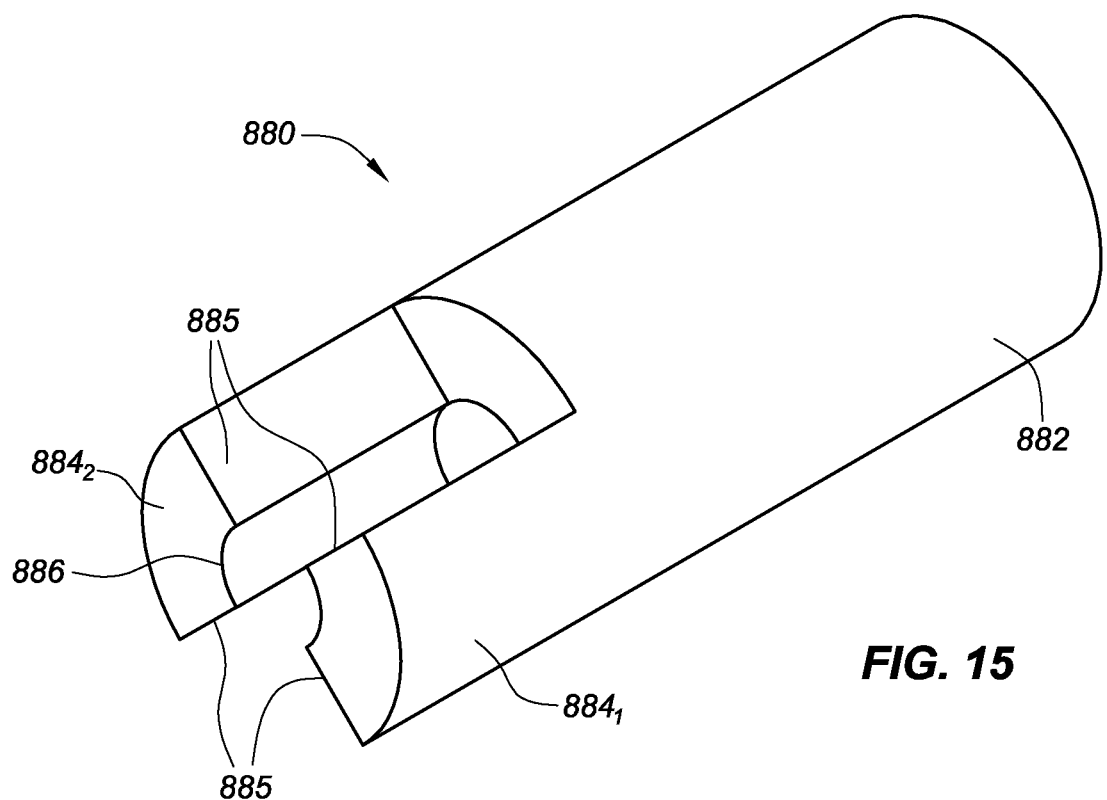
FIG. 15 is an isometric view of a core having a body and projections extending therefrom according to another embodiment of the disclosure.
Figure 15A:
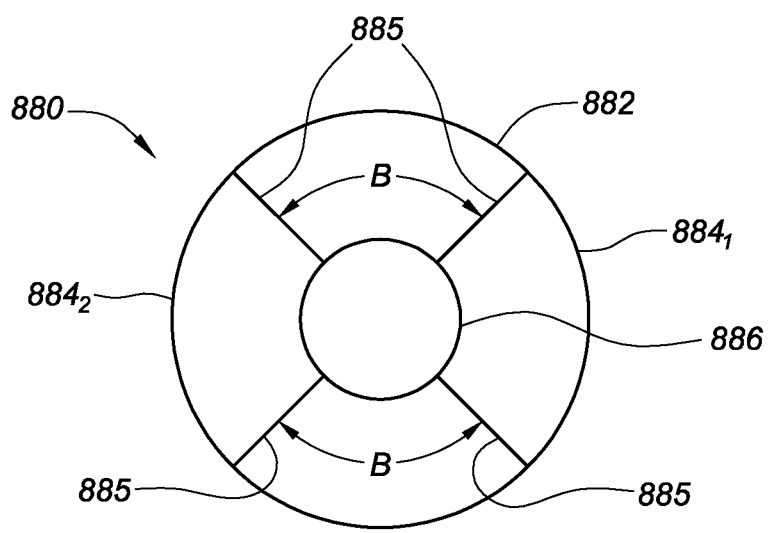
FIG. 15A is a view of the left end (as oriented in FIG. 15) of the core illustrated in FIG. 15.

FIGS. 15 and 15A show a core 880 comprising a body 882 from which one or more projections 884$_1$, 884$_2$ having a sector or pie-shaped cross-section extend therefrom. A lumen 886 is shown extending through core 880. As shown (for example only and without limitation), each sector or pie shaped projection $884_1$, $884_2$ may sweep across an angle of about 90 degrees. That is, the sector or pie shaped projections $884_1$, $884_2$ are smaller than sector or pie-shaped projections $784_1$, $784_2$ as shown in FIGS. 14 and 14A. Each projection provides two landing areas 885 at which an electrical connection between a coil and a conductor may be made as described in greater detail elsewhere herein. Although larger than areas A of core 780 of FIGS. 14 and 14A, the areas B between sector or pie shaped projections $884_1$, $884_2$, still provide protection for the landing areas 885, and any electrical connection located thereon, from physical disruption. The larger size of areas B may provide greater access to landing areas 885 to allow for easier construction and electrical connection of a position sensor incorporating core 880, as compared to core 780.

Figure 16A:
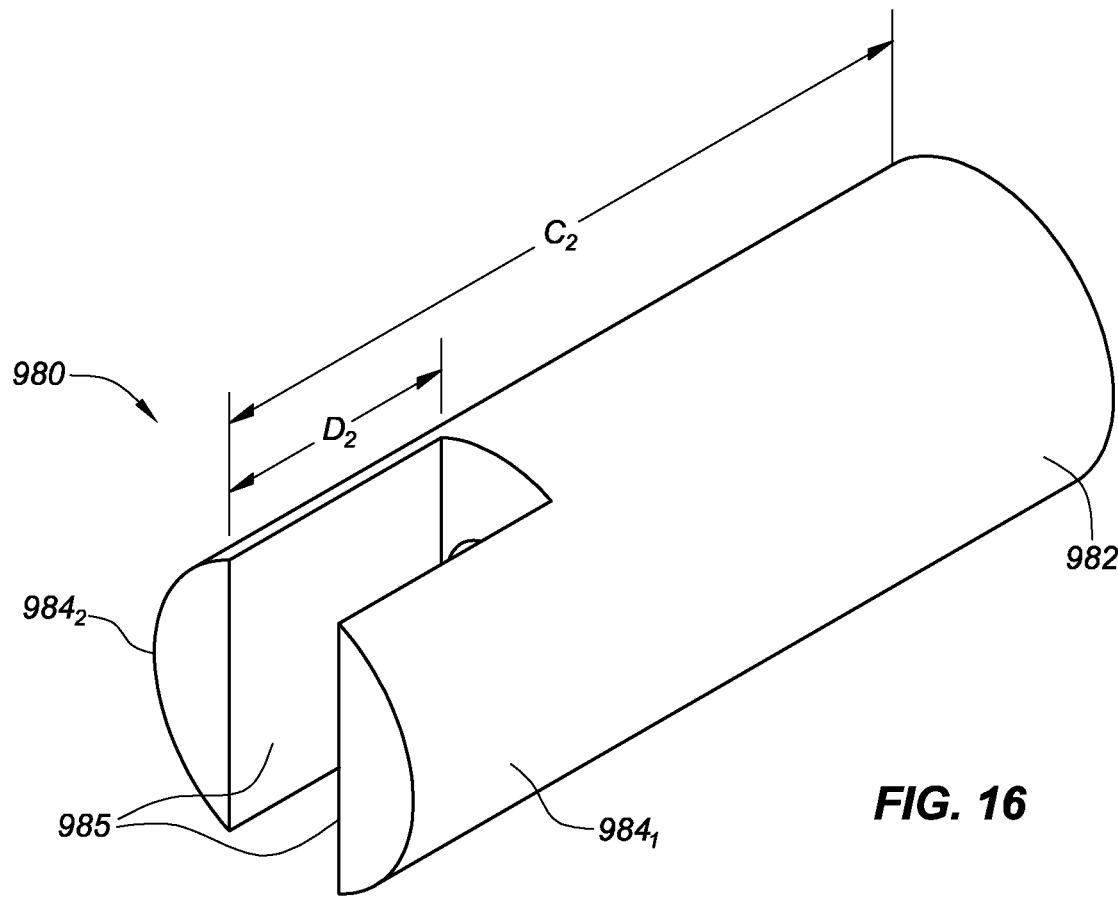
FIG. 16A is a view of the left end (as oriented in FIG. 16) of the core illustrated in FIG. 16.
Figure 16A:
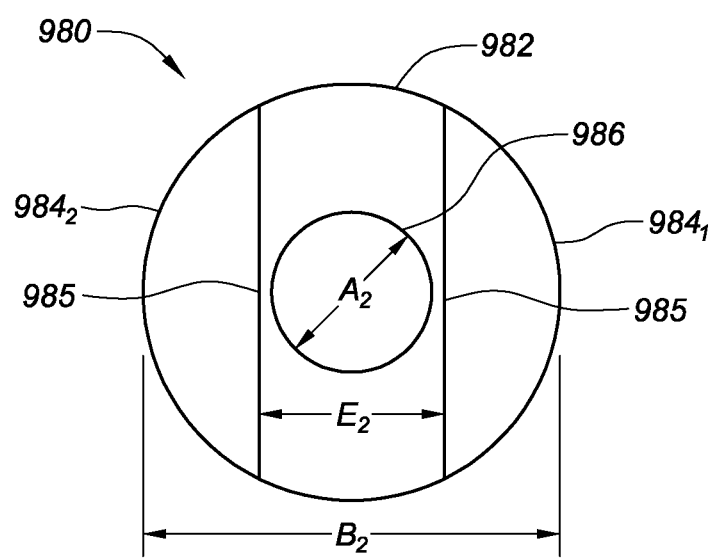

FIGS. 16 and 16A show a core 980 comprising a body 982 from which one or more projections $984_1$, $984_2$ having a circular segment-shaped cross-section extend therefrom. A lumen 986 is shown extending through core 980. As shown (for example only and without limitation), each circular segment shaped projection $984_1$, $984_2$ sweeps across an angle of about 180 degrees. Each projection provides two landing areas 985 at which an electrical connection between a coil and a conductor may be made as described in greater detail elsewhere herein. Area $E_2$ between circular segment-shaped projection $984_1$, $984_2$, provides protection for the landing areas 985, and any electrical connection located thereon, from physical disruption.

With continued reference to FIGS. 16 and 16A, exemplary dimensions (and without limitation) for the position sensors described herein are shown. Lumen 986 may have a diameter $A_2$ of about 0.0020" (about 0.0508 mm) to about 0.0040" (about 0.1016 mm) (e.g., about 0.0020" (about 0.0508 mm), about 0.0025" (about 0.0635 mm), about 0.0030" (about 0.0762 mm), about 0.0035" (about 0.0889 mm), and about 0.0040" (about 0.1016 mm)). Core 980 may have an outer diameter $B_2$ of about 0.0060" (about 0.1524 mm) to about 0.0080" (about 0.2032 mm) (e.g., about 0.0060" (about 0.1524 mm), about 0.0065" (about 0.1651 mm), about 0.0070" (about 0.1778 mm), about 0.0075" (about 0.1905 mm), and about 0.0080" (about 0.2032 mm)). Core 980 may have a length $C_2$ of about 0.5 mm to about 7.0 mm in length (e.g., about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, and about 7.0 mm). Projections $984_1$, $984_2$ may have length $D_2$ of about 0.05 mm to about 2.0 mm in length (e.g., about 0.05 mm, about 0.1 mm, about 1.0 mm, about 1.5 mm, and about 2.0 mm). Projections $984_1$, $984_2$ may be located a distance $E_2$ from one another of less than about 0.005" (about 0.127 mm) (e.g., about 0.003" (about 0.0762 mm), about 0.004" (about 0.1016 mm), and about 0.005" (about 0.127 mm). In an embodiment (for example only and without limitation), core 980 has the following dimensions: $A_2$=0.0030"+0.0005"/-0.000" (0.0762 mm+0.0127 mm/-0.0000 mm); $B_2$=0.0070"+0.000"/-0.0005" (0.1778 mm+0.0000 mm/-0.0127 mm), $C_2$=3.0 mm; $D_2$=1.0 mm; and $E_2 \leq 0.005$" (0.127 mm).

Figure 17:
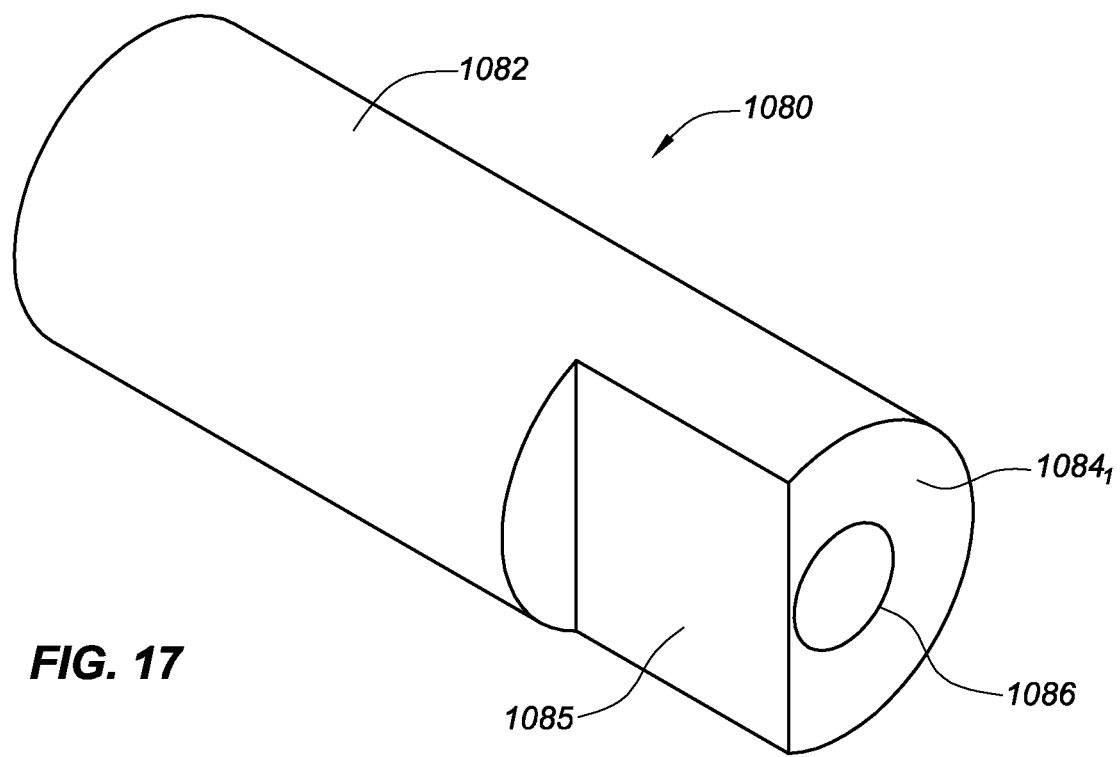
FIG. 17 is an isometric view of a core having a body and a projection extending therefrom according to another embodiment of the disclosure.
Figure 17A:
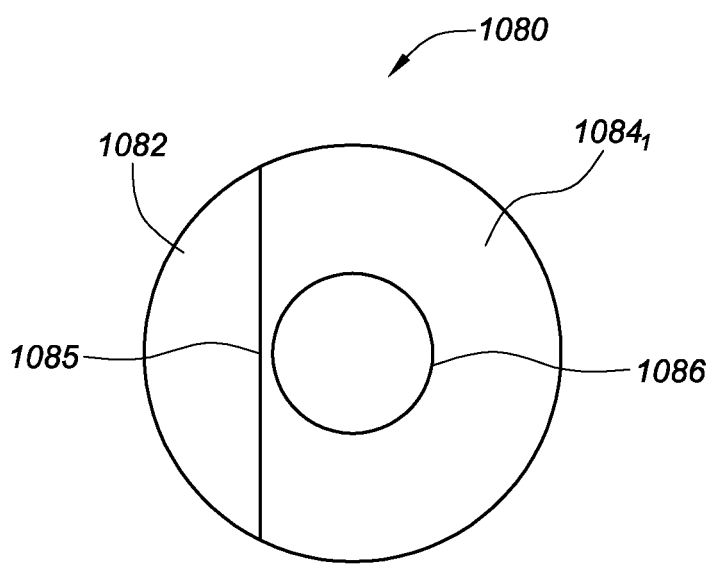
FIG. 17A is a view of the right end (as oriented in FIG. 17) of the core illustrated in FIG. 17.

FIGS. 17 and 17A show a core 1080 comprising a body 1082 from which a single projection $1084_1$ having a substantially D-shaped cross-section extends therefrom. The single substantially D-shaped projection $1084_1$ is shown as larger in cross-sectional area than a half-circle and has the geometry of what remains from a circle when a circle segment is removed. Thus, projection $1084_1$ may have a much larger cross-sectional area than other projections, which may result in increased magnetic flux, and therefore higher induced voltage in a position sensor, compared with other projections. A lumen 1086 is shown extending through core 1080. The substantially D-shaped projection provides a single landing area 1085 at which an electrical connection between a coil and a conductor may be made as described in greater detail elsewhere herein.

Figure 18:
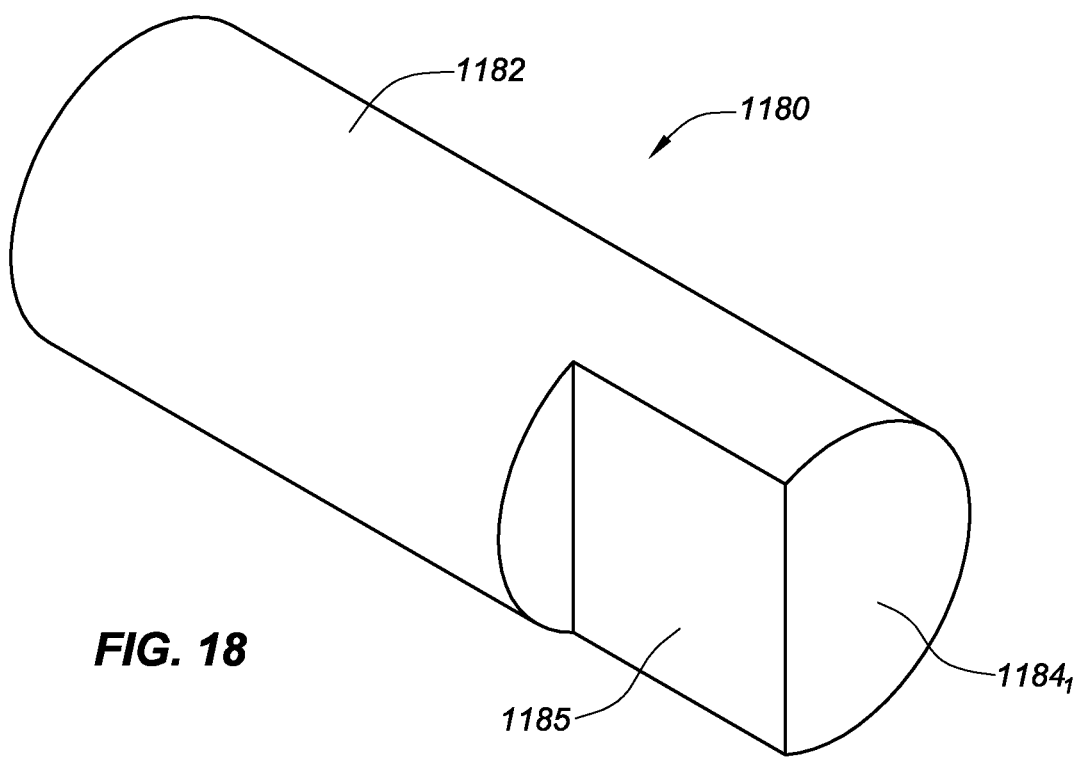
FIG. 18 is an isometric view of a core having a body and a projection extending therefrom according to another embodiment of the disclosure.
Figure 18A:
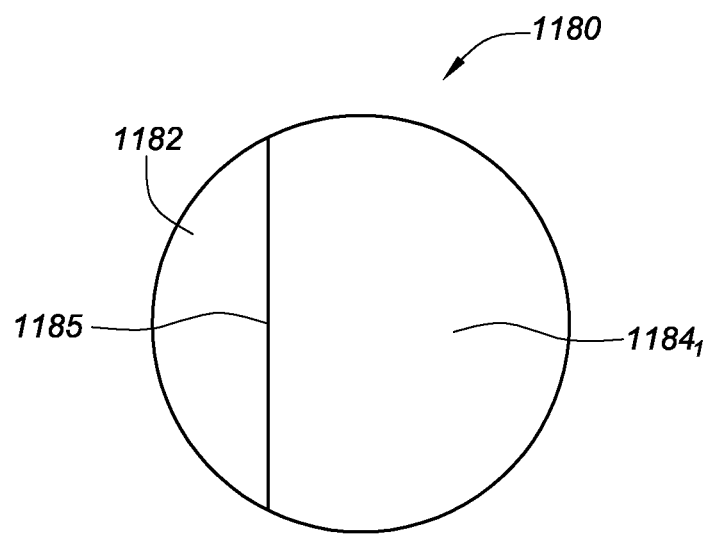
FIG. 18A is a view of the right end (as oriented in FIG. 18) of the core illustrated in FIG. 18.

FIGS. 18 and 18A show a core 1180 comprising a body 1182 from which a single projection $1184_1$ having a substantially D-shaped cross-section extends therefrom. Core 1180 is substantially similar to core 1080, except that core 1180 does not include a lumen extending through core 1180. The D-shaped projection $1184_1$ provides a single landing area 1185 at which an electrical connection between a coil and a conductor may be made as described in greater detail elsewhere herein.

Figure 19:
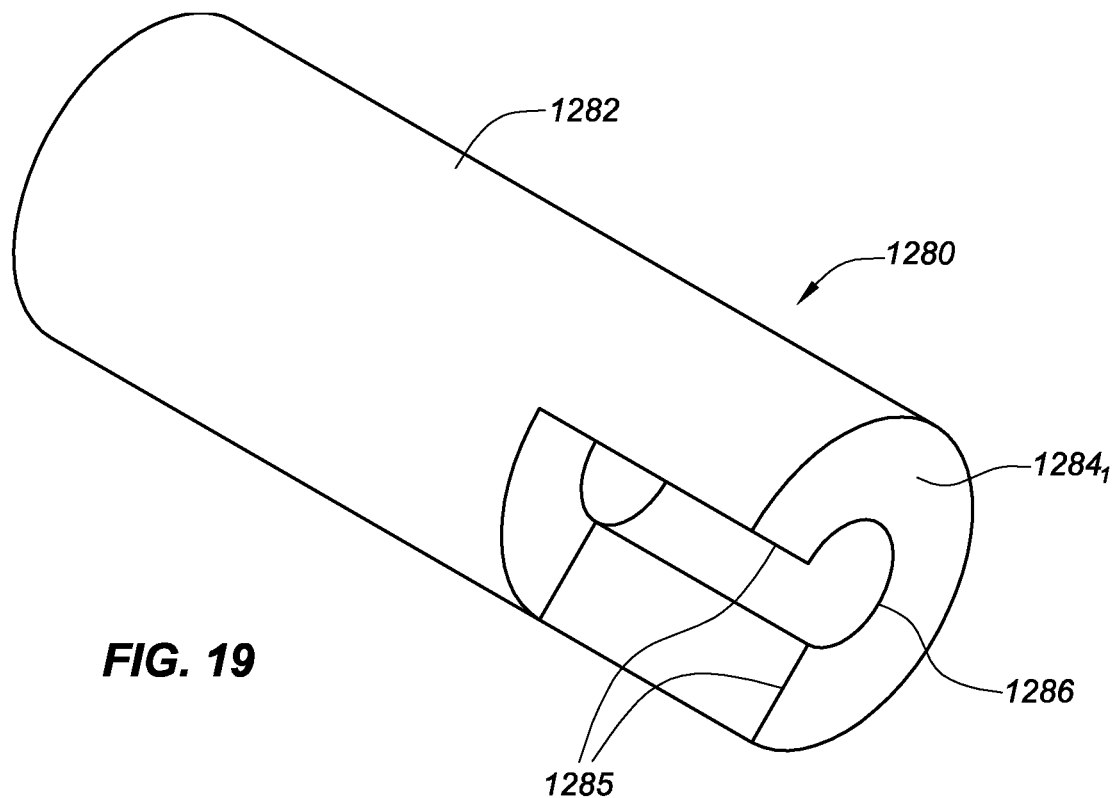
FIG. 19 is an isometric view of a core having a body and a projection extending therefrom according to another embodiment of the disclosure.
Figure 19A:
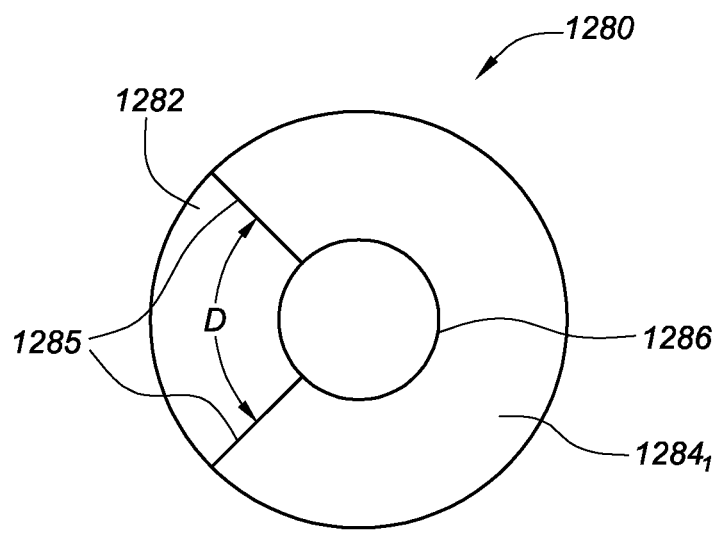
FIG. 19A is a view of the right end (as oriented in FIG. 19) of the core illustrated in FIG. 19.

FIGS. 19 and 19A show a core 1280 comprising a body 1282 from which a single major-sector shaped projection $1284_1$ extends therefrom. A lumen 1286 is shown extending through core 1280. As shown (for example only and without limitation), the major-sector shaped projection $1284_1$ sweeps across an angle of greater than 180 degrees. Major-sector shaped projection $1284_1$ provides two landing areas 1285 at which an electrical connection between a coil and a conductor may be made as described in greater detail elsewhere herein. Area D between the two landing areas 1285 provides protection for the landing areas 1285, and any electrical connection located thereon, from physical disruption.

Figure 20:
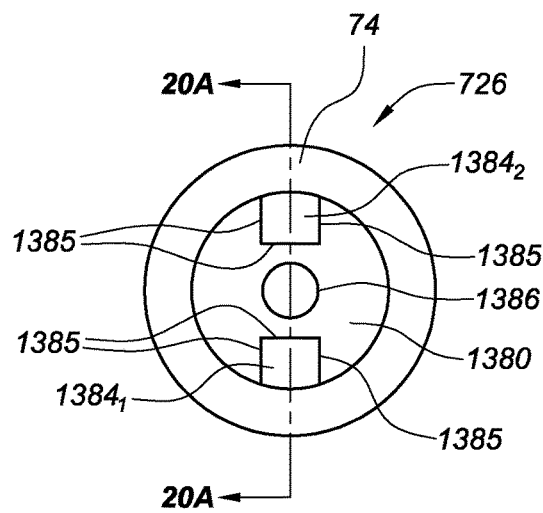
FIG. 20 is an end view of a magnetic position sensor according to another embodiment of the disclosure.
Figure 20A:
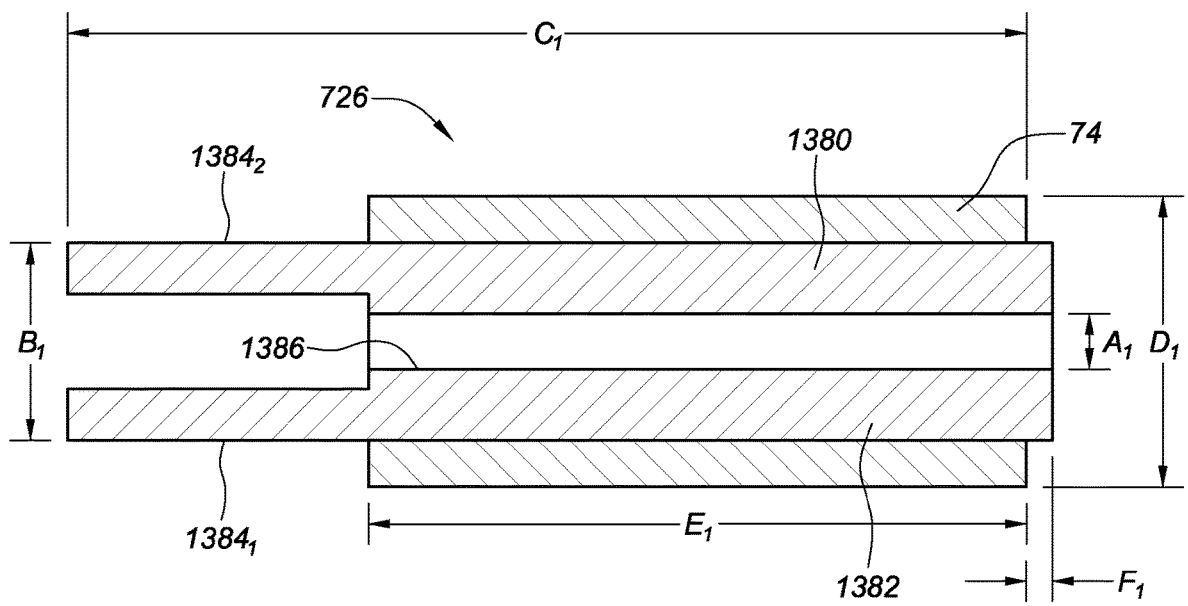
FIG. 20A is a cross-sectional view of a portion of the magnetic position sensor illustrated in FIG. 20 taken along line 20A-20A.

While projections shown and described herein extend to the lumen extending through core, in various embodiments the projections may not extend all the way to the lumen or may not be in tangential contact with the lumen. For example only and without limitation, FIGS. 20 and 20A show a position sensor 726 having coil 74 around a core 1380, where core 1380 comprises a body 1382 from which one or more substantially square-shaped projections $1384_1$, $1384_2$ extend therefrom. A lumen 1386 is shown extending through core 1380. Projections $1384_1$, $1384_2$ do not extend all the way to lumen 1386. Accordingly, each projection may provide three landing areas 1385 at which an electrical connection between coil 74 and a conductor may be made as described in greater detail elsewhere herein. Thus, it will be understood that in various embodiments, each of the projection geometries described herein may not extend all the way to the lumen extending through the core.

With continued reference to FIG. 20A, exemplary dimensions (and without limitation) for the position sensors described herein are shown. Lumen 1386 may have a diameter $A_1$ of about 0.0020" (about 0.0508 mm) to about 0.0040" (about 0.1016 mm) (e.g., about 0.0020" (about 0.0508 mm), about 0.0025" (about 0.0635 mm), about 0.0030" (about 0.0762 mm), about 0.0035" (about 0.0889 mm), and about 0.0040" (about 0.1016 mm)). Core 1380 may have an outer diameter $B_1$ of about 0.0060" (about 0.1524 mm) to about 0.0080" (about 0.2032 mm) (e.g., about 0.0060" (about 0.1524 mm), about 0.0065" (about 0.1651 mm), about 0.0070" (about 0.1778 mm), about 0.0075" (about 0.1905 mm), and about 0.0080" (about 0.2032 mm)). Core 1380 may have a length $C_1$ of about 0.5 mm to about 7.0 mm in length (e.g., about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, about 6.5 mm, about 7.0 mm). Coil 74 may have an outer diameter $D_1$ of about 0.01" (about 0.254 mm) to about 0.02" (about 0.508 mm) (e.g., about 0.01" (about 0.254 mm), about 0.0108" (about 0.274 mm), about 0.015" (about 0.381 mm), and about 0.02"

(about 0.508 mm)). Coil 74 may have a length $E_1$ of about 1.0 mm to about 2.0 mm (e.g., about 1.0 mm, about 1.5 mm, about 1.9 mm, and about 2.0 mm). In various embodiments (for example only and without limitation), coil 74 may be located on core 1380 such that body 1382 of core 1380 may stick out slightly. This stick out may occur during the manufacture of certain position sensors, wherein the stick out portion of body 1382 is held as the wires 76 of coil 74 are wound around core 1380. In embodiments were the stick out is present, the length $F_1$ of the stick out may be about 0.01 mm to about 0.15 mm (e.g., about 0.01 mm, about 0.05 mm, about 0.10 mm, and about 0.15 mm). It will be understood that in other embodiments, the position sensor has no such stick out of the body of the core. In an embodiment (for example only and without limitation), position sensor 726 has the following dimensions: $A_1$=0.0030"+0.0005"/−0.000" (0.0762 mm+0.0127 mm/−0.0000 mm); $B_1$=0.0070"+0.000"/−0.0005" (0.1778 mm+0.0000 mm/−0.0127 mm), $C_1$=3.0 mm; $D_1 \leq 0.0108$" (0.274 mm); $E_1$=1.9 mm; and $F_1 \leq 0.1$ mm.

Figure 21:
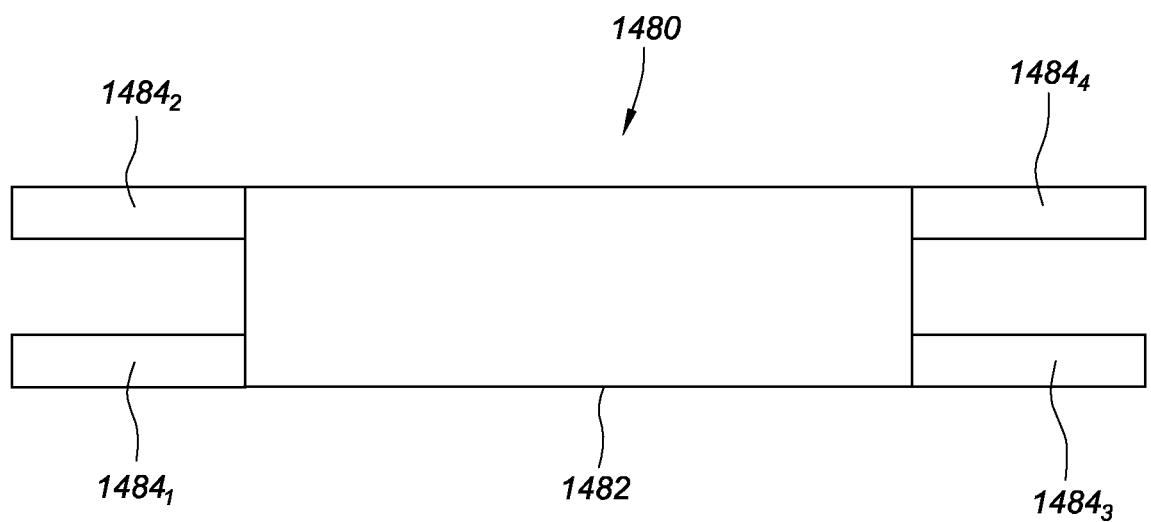
FIG. 21 is a side view of a core according to another embodiment of the disclosure.

Now with reference to FIG. 21, core 1480 comprises a body 1482 from which one or more projections 1484$_1$, 1484$_2$, 1484$_3$, 1484$_4$ extend from both opposite ends of body 1482. That is, projections 1484$_1$, 1484$_2$ extend from a first end of body 1482 and projections 1484$_3$, 1484$_4$ extend from a second end of body 1482. The inclusion of projections 1484$_1$, 1484$_2$, 1484$_3$, 1484$_4$ extending from both opposite ends of body 1482 may result in an increased magnetic flux, and therefore higher induced voltage in a position sensor, compared with embodiments of cores only having projections extending from one end of body 1482.

The cores described herein can be made of any material, with materials of higher magnetic permeability being more suitable. Magnetic field lines preferentially travel through materials with high permeability. In various embodiments, μ-metals, amorphous metal alloys (also known as metallic glass alloys), nanocrystalline metals or 99.95% pure iron may be used. One particular branch of Mu metals and Metglas® amorphous alloys (METGLAS is a registered trademark of Metglas, Inc. of Conway, S.C.) are both particularly well suited for use with cores of the present disclosure. As compared to air with a magnetic permeability equal to one (i.e., μ=1), it has been found that Mu metals have a relative magnetic permeability of approximately 50,000, 99.95% pure iron has a relative magnetic permeability of approximately 200,000.

"Magnetic permeability" as used herein, unless indicated to the contrary, refers to the ability of a material or element to support the formation of a magnetic field within itself. It is the degree of magnetization that a material obtains in response to an applied magnetic field. A material with a "high permeability" or "high magnetic permeability" as used herein, unless indicated to the contrary, means any material having a relative magnetic permeability above the relative magnetic permeability of Martensitic stainless steel.

Although it is desired to use high magnetic permeability materials for the cores described herein, it will be understood that in other embodiments (for example only and without limitation) that the cores described herein may be made of non-high magnetic permeability materials, including but not limited to, various metals, plastics, ceramics or glass. With the use of non-high magnetic permeability materials for various embodiments of the cores described herein, the increase signal strength provided by the projections extending from the core may be reduced or eliminated. However, the projections will still provide one or more landing areas where a protected electrical connection may be made between the coil and the conductor. Therefore, such cores will still provide increased electrical and/or mechanical integrity of the position sensor as compared to prior art position sensors.

Although various embodiments of positions sensors described herein utilize coil 74 comprising a wire winding 76, in other embodiments, the position sensors described herein may comprise coils of other configurations made by, for example, additive manufacturing methods. For example only and without limitation, in various embodiments, the coil may be comprised of conductive and nonconductive materials which may be an electrically conductive ink or electrically nonconductive ink, respectively. The conductive and nonconductive materials may be formed by depositing or printing directly on a surface, such as a substrate or on one of the cores described herein, and directly over pre-existing layers of existing conductive and nonconductive materials. The conductive and nonconductive materials may be formed directly on a substrate or on one of the cores described herein using technologies such as ink jet printing, pad printing, aerosol jet deposition that may be known in the art as aerosol jet printing (AJP), three-dimensional (3D) microprinting, and other printing technologies as known to those of skill in the art. The three dimensional layering of conductive and nonconductive materials may be formed in a predetermined pattern and/or configuration to provide end-to-end electrical connectivity.

For example, an alternative embodiment of a coil 174 for use in with cores described herein is shown and described with reference to FIGS. 22-25. It will be understood that coil 174 can be used with any core 80, 180, 280, 380, 480, 580, 680, 780, 880, 980, 1080, 1180, 1280, 1380, 1480 described herein without departing from the scope of the disclosure.

FIG. 22 is a top view of a coil 174, which, in conjunction with one of the cores described herein may be used as position sensor 26 in the medical device 12 shown in FIG. 1. Coil 174 is shown in a preliminary stage of manufacture (i.e., a "flat" pattern). After further processing, coil 174 in final form may be wrapped around one of the cores described herein. Coil 174 comprises flexible printed circuitry, as described in greater detail below and in greater detail in U.S. Patent Publication No. 2013/0066194 published on Mar. 14, 2013, to Seter, the entire content of which is hereby incorporated herein by reference in its entirety for all purposes and as though fully set forth herein. As shown, coil 174 includes an electrically insulative, relatively flexible substrate 148 and an electrically conductive trace 150*a* disposed (i.e., "printed") on a first surface of substrate 148. It should be understood, however, that a flat pattern is exemplary only and not limiting in nature. Alternate embodiments may include additional approaches for forming conductive traces on a substrate, now known or hereafter developed, including forming such traces on non-flat substrates, for example, round or curved surfaces (i.e., three-dimensional in nature).

Substrate 148 may be generally rectangular in shape, having a longitudinal direction (i.e., long dimension) and a transverse direction (i.e., shorter dimension). As shown, substrate 48 has corners designated A, B, C and D. It should be understood, however, that the substrate may take a wide range of shapes and sizes, depending upon the determined trace pattern and sensor final form, as described in greater detail below.

Trace 150*a* is arranged in a pattern configured to create a sensor 826 when substrate 148 is folded or formed into a final shape (best shown in FIGS. 24 and 25) around the body one of the cores described herein. Trace 150*a* includes a start lead 154 and an end lead 156, which leads are configured to provide a signal that is coupled to MPS 24. Trace 150a is electrically continuous between the start and end leads 154, 156. It should be understood that "start" and "end" designations are exemplary only and not limiting in nature. Further, although trace 150a is shown arranged such that both leads 154, 156 appear at the same longitudinal end (e.g., the longitudinally-proximal end of coil 174), other variations are possible (e.g., both leads can appear at the longitudinally distal end of coil 174, or leads 154, 156 can appear at respective proximal and distal ends of coil 174). As shown, at least a portion of trace 150a is arranged and disposed on substrate 148 in a generally serpentine pattern, including a plurality of advancing sections 158, a plurality of returning sections 159, and a plurality of intervening bridge sections 160. The advancing and returning sections 158, 159 are generally transverse diagonals relative to substrate 148, are parallel to each other, and are separated from each other by a predetermined spacing 162. As shown, spacing 162 is constant across the trace pattern. As further shown, the advancing and returning sections 158, 159 may be arranged at an angle α relative to a true transverse reference line. The angle α may be selected to facilitate formation of coil 174 when the substrate is folded.

In an embodiment, the predetermined spacing 162 may be less, and preferably much less, than a width of trace taken in the longitudinal direction, thereby defining a relatively low pitch (i.e., the spacing 162 between trace sections is relatively small compared to the width of the trace itself). In an embodiment, the width of trace 150a may be on the order of about several microns, while the predetermined spacing may be less than about five microns. It should be understood, however, that a wide range of configurations are possible in terms of trace width, spacing (i.e., spacing 162), angle α, number of advancing and returning sections, number of layers having electrically-conductive traces, and the like, in accordance with desired detection characteristics.

FIG. 23 is a cross-sectional view of coil 174 taken substantially along lines 23-23 in FIG. 22. As shown, substrate 148 has a predetermined thickness, which may be on the order of several microns. Substrate 148 may comprise conventional materials known in the art for use in flexible printed circuitry, such as a flexible plastic material selected from the group comprising polyimide, polyetheretherketone (PEEK), polyester, polyethylene terephthalate or a combination thereof. In some embodiments, substrate 148 may comprise KAPTON™ or MYLAR™ material commercially available from E.I. du Pont de Nemours and Company. It should be understood that variations are possible. The electrically-conductive trace 150a may comprise an electrically-conductive material, such as copper, although other electrically-conductive materials, such as platinum or gold, or combinations thereof (e.g., copper plated with platinum, gold, or silver) may be possible depending on the desired electrical characteristics. Conventional approaches and materials may be used for forming ("printing") a suitable pattern (trace 150a) on substrate 148. Moreover, although not shown, an over-layer of electrically-insulating material may be disposed over the electrically conductive trace pattern 150a.

FIG. 24 is an isometric view of the coil 174 of FIG. 22, wrapped, folded, or otherwise formed around the body of a core (shown, for example only and without limitation, as core 80 described in greater detail elsewhere herein) to produce position sensor 826. In this embodiment, the folded coil 174 extends longitudinally along an axis 166. It should be understood, however, that other shapes are possible (e.g., oval shape in radial cross section). Coil 174 thus formed is responsive to a changing magnetic field passing through the projected area of position sensor 126. In this regard, position sensor 126 will detect one or more characteristics of such field(s) and generate a signal indicative thereof.

A method of fabricating a miniature electromagnetic coil using flexible printed circuitry includes a number of steps. The first step involves providing an electrically insulative substrate, for example, as described above. The next step involves producing an electrically-conductive trace on the substrate in a predetermined pattern, for example, also as described above. The next steps involve folding the flexible substrate into the desired shape around one of the cores (described in greater detail elsewhere herein) and then fixing the substrate in that shape. In one embodiment, the fixing step may involve adhering longitudinally-extending edges, one to another, for example, adhering edges BD and AC together. This step couples corner C to corner D and corner A to corner B. This step is operative to mechanically couple edges BD and AC, thereby fixing the substrate into the desired shape. In other embodiments (for example only and without limitation), the fixing step may involve adhering the substrate to body 82 of core 80. The fixing step may be performed in accordance with conventional techniques, including without limitation micro-welding, micro-soldering, micro-gluing through the use of micro-vias, adhering using adhesives or tapes, and the like.

FIG. 25 is an enlarged, isometric view of FIG. 24, showing, in greater detail, sensor 826. The configuration of the trace pattern is such that when the substrate 148 is folded into the desired shape around body 82 of core 80, the bridge sections 160 generally face each other. In final form, trace 150a produces has a three-dimensional, spiral coil substantially enclosing body 82 of core 80. Sensor 826 includes a plurality of turns between the start and end leads. Sensor 826 is thus configured to function as a micro-electromagnetic sensing coil (sensor).

As further shown in FIG. 25, trace 150a can be configured so that start and end leads 154, 156 are located at a single longitudinal end of sensor 826 (e.g., proximal end) in the final configuration, and where leads 154, 156 terminate on projections $84_1$, $84_2$ of core 80 where coil 174 may be electrically connected to leads $63_1$, $63_2$ of conductor 62, for example only and without limitation, using one of the variety of electrical connections described herein with respect to FIGS. 4, 5, 5A, 7, 7A, 8, 8A, 9, 9A, 10, 11, 12, and 13, such as for example only and without limitation, conductive elements 90.

For example, an alternative embodiment of a coil 274 for use in with cores described herein is shown and described with reference to FIGS. 26-27. It will be understood that coil 274 can be used with any core 80, 180, 280, 380, 480, 580, 680, 780, 880, 980, 1080, 1180, 1280, 1380, 1480 described herein without departing from the scope of the disclosure.

Figure 26:
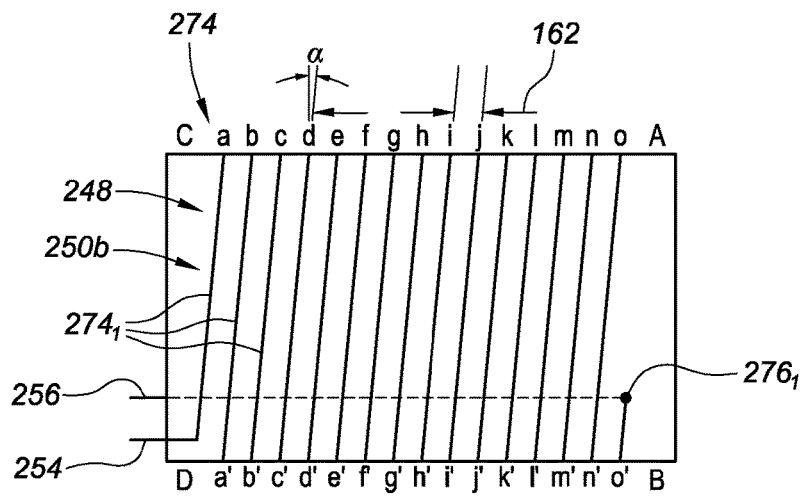
FIG. 26 is a top view of a printed coil formed using flexible printed circuitry for use in the embodiments of magnetic position sensors described herein.

FIG. 26 is a top view of a coil 274, which, in conjunction with one of the cores described herein may be used as position sensor 26 in the medical device 12 shown in FIG. 1. Coil 274 is shown in a preliminary stage of manufacture (i.e., a "flat" pattern). Unless other stated, the coil 274 may be the same as coil 174 described above, and may be configured into a position sensor 926 in the same fashion as was used to configure coil 174 into a position sensor 826.

The coil 274 includes a substrate 248 and a trace pattern 250b that includes a plurality of advancing sections $274_1$. Trace 250b can be generally of the same configuration as trace 150a, except as described below. Sections $274_1$ of trace pattern 250b are initially electrically separate but are later electrically connected to form the electrically continuous windings of sensor 926 when the substrate 248 is folded.

Figure 27:
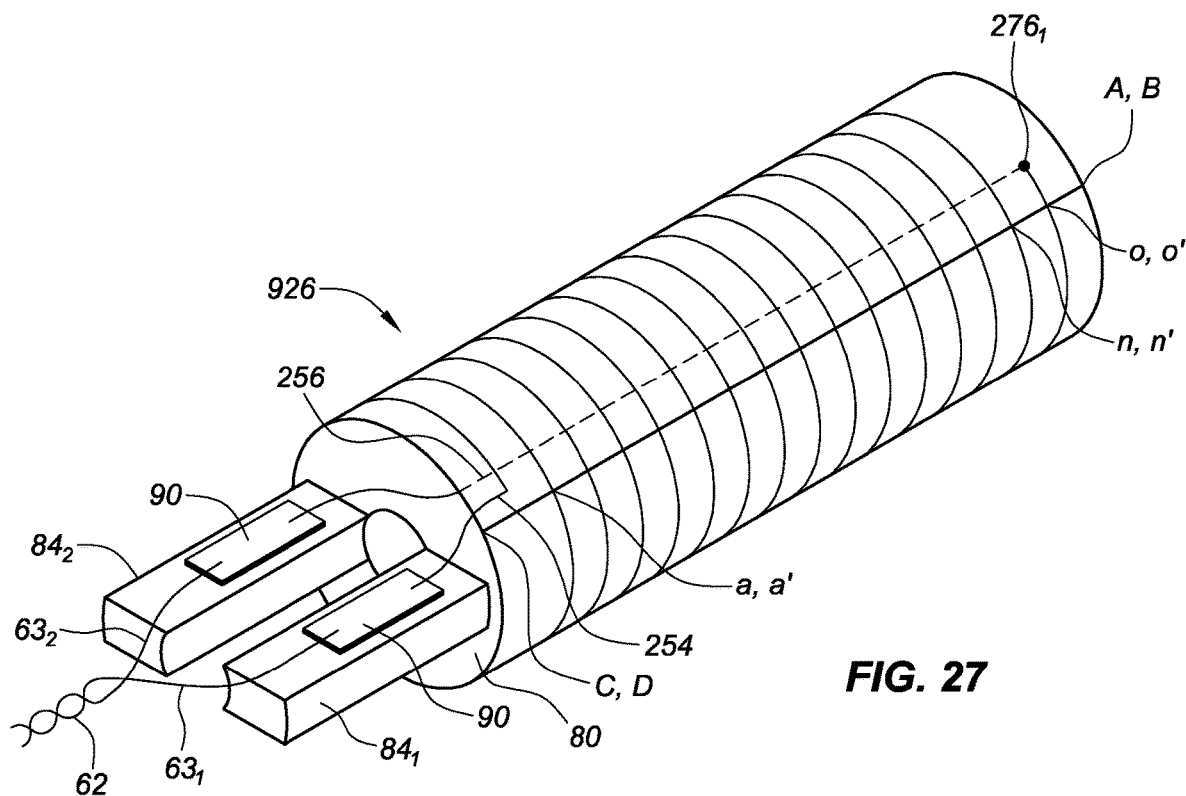
FIG. 27 is an isometric view of a magnetic position sensor utilizing the printed coil illustrated in FIG. 26 according to another embodiment of the disclosure.

FIG. 27 is an isometric view of the coil 274 of FIG. 26, wrapped, folded, or otherwise formed into a desired, final shape around the body one of the cores described herein to produce sensor 926. The connection concept involves aligning points a-a', b-b' and so on, and then electrically connecting the separate sections $274_1$ at points a-a', b-b' and so on. A position sensor 926 results after all the individual sections $274_1$ have been electrically connected, as described above. The start and end leads are designated 254, 256, respectively. Just as with position sensor 826, the start and end leads 254, 256 terminate on projections $84_1$, $84_2$ of core 80 where coil 274 may be electrically connected to leads $63_1$, $63_2$ of conductor 62, for example only and without limitation, using one of the variety of electrical connections described herein with respect to FIGS. 4, 5, 5A, 7, 7A, 8, 8A, 9, 9A, 10, 11, 12, and 13, such as for example only and without limitation, conductive elements 90.

As with the embodiment of FIGS. 22-25, the end lead 256 can be disposed on at the same axial end of the position sensor 926 as the start lead 254. This can be accomplished by electrically insulating the returning end lead with respect to the "windings" (sections $274_1$) across or over which it passes to reach the same end as the start lead 254. In the illustrative embodiment, the end lead 256 is passed through a via $276_1$ and is routed on the opposing side of substrate 248 (i.e., opposite the side on which sections $274_1$ are formed). Alternatively, return/end lead 256 can run across sections $274_1$, provided, however, that return/end lead 256 is properly, electrically, insulated. The position sensor 926 includes a plurality of turns between the start and end leads.

In other embodiments, magnetic field sensitivity (pick-up intensity) can be increased by adding an increased number of windings, for example, by including additional layers to the printed circuit board (i.e., each layer contributing a certain number of "windings" formed by sections $274_1$, and which can be electrically connected to winding formed on upper and lower layers in ways known in the art).

Figure 28A:
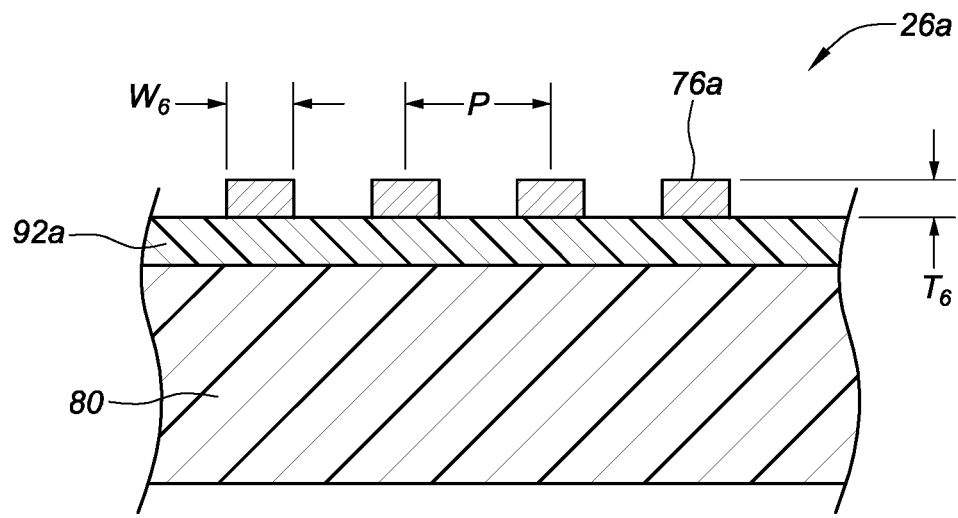
FIG. 28A is a cross-sectional view of a magnetic position sensor according to another embodiment of the disclosure.
Figure 28B:
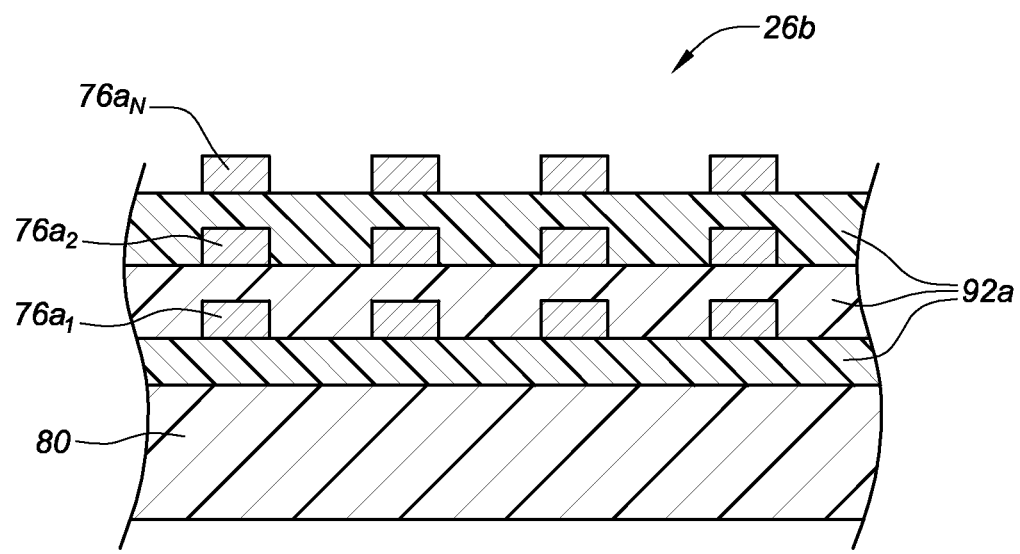
FIG. 28B is a cross-sectional view of a magnetic position sensor according to another embodiment of the disclosure.

In yet other embodiments (for example only and without limitation), the coil may be printed, formed or otherwise deposited directly on embodiments of the cores described herein, as described in greater detail below and in greater detail in U.S. Patent Publication No. 2015/0374254 published on Dec. 31, 2015 to Sobe, the entire content of which is incorporated herein by reference in its entirety for all purposes and as though fully set forth herein. FIGS. 28A and 28B are enlarged, partial cross-sectional views, with portions broken away, of embodiments of the position sensor 26 of FIG. 2, designated position sensors 26a and 26b, respectively. Position sensors 26a, 26b, may be disposed proximate the distal end of medical device 12.

FIG. 28A shows position sensor 26a, which includes core 80 (or any one of the other cores described in greater detail elsewhere herein). An insulative layer 92a, which comprises electrically nonconductive material, may be directly formed on core 80 by printing or other ink deposition technologies as known to those with skill in the art. A single layer coil 76a may be formed on the insulative layer 92a in a predefined pattern. In another embodiment, when core 80 comprises nonconductive material, the single layer coil 76a may be formed directly onto core 80 without need for the insulative layer 92a and may comprise electrically conductive material. The pattern may be generally spiral shaped around core 80. In an exemplary and non-limiting embodiment, the single layer coil 76a may have a width $W_6$ from about 0.0059 mm to about 0.060 mm and a thickness $T_6$ from about 0.001 mm to about 0.003 mm. In an exemplary and non-limiting embodiment, the single layer coil 76a has a distance between the conductor material as it spirals about core 80, also known as a pitch P, from about 0.005 mm to about 0.060 mm. In an exemplary and non-limiting embodiment, the single layer coil 76a may have a skew angle α as the conductor material spirals about the coil of about up to 45 degrees (skew angle α is generally illustrated in FIG. 22).

FIG. 28B shows the position sensor 26b, which has a plurality of layers, designated $76a_1$, $76a_2$, ..., $76a_N$ wherein N=the number of layers in the position sensor 26b, and which comprises electrically conductive material. Each layer $76a_{1-N}$ of position sensor 26b may be separated by a respective insulative layer 92a.

In an embodiment, the conductive and nonconductive materials may be an electrically conductive ink or electrically nonconductive ink, respectively. The conductive and nonconductive materials may be formed by depositing or printing directly on a surface, such as body 82 and/or projections $84_1$, $84_2$ of core 80, and directly over pre-existing layers of existing conductive and nonconductive materials. The conductive and nonconductive materials may be formed directly on body 82 and/or projections $84_1$, $84_2$ of core 80 using technologies such as ink jet printing, pad printing, aerosol jet deposition that may be known in the art as aerosol jet printing (AJP), three-dimensional (3D) microprinting, and other printing technologies as known to those of skill in the art.

The single layer coil 76a or multiple layer coil $76a_{1-N}$ include leads (not shown) which terminate on projections $84_1$, $84_2$ of core 80 where the single layer coil 76a or multiple layer coil $76a_{1-N}$ may be electrically connected to leads $63_1$, $63_2$ of conductor 62, for example only and without limitation, using one of the variety of electrical connections described herein with respect to FIGS. 4, 5, 5A, 7, 7A, 8, 8A, 9, 9A, 10, 11, 12, and 13.

While various embodiments of position sensors using various core designs have been shown and described for use in medical devices, in particular an ablation catheter as shown in FIG. 2, it will be understood that in various other embodiments, position sensors having the described cores 80, 180, 280, 380, 480, 580, 680, 780, 880, 980, 1080, 1180, 1280, 1380, 1480 may be used in a variety of medical devices including, but not limited to, catheters, guide wires, and introducers. For example only and without limitation, position sensors 26 having core 80 with projections $84_1$, $84_2$ may be used in the guide wires known in the art.

Figure 29:
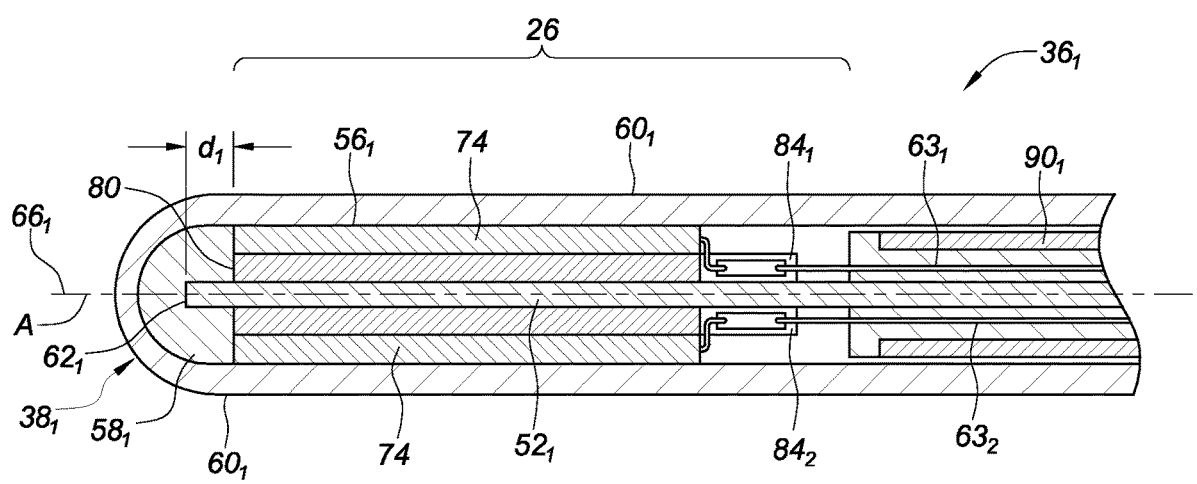
FIG. 29 is a cross-sectional view of a magnetic position sensor in a guidewire according to another embodiment of the disclosure.

Now with reference to FIG. 29, an embodiment of position sensor 26 having core 80 with projections $84_1$, $84_2$ located in a distal end $38_1$ of a guidewire $36_1$ is shown and described. Additional features and aspects of guidewire $36_1$ are described in greater detail in U.S. Pat. No. 9,364,640, issued on Jun. 14, 2016 to Vanney et al., the entire content of which is hereby incorporated herein by reference in its entirety for all purposes and as though fully set forth herein. Guidewire $36_1$ may be used as the medical device 12 in system 10 (FIG. 1). Guidewire $36_1$ is generally elongate and extends along a central longitudinal axis designated "A" between a guidewire distal end $38_1$ and a guidewire proximal end (not shown). Guidewire $36_1$ includes central corewire $52_1$, position sensor 26, a shroud $56_1$, a plug $58_1$, and a coating $60_1$. As described in greater detail elsewhere herein, position sensor 26 has an output signal useful for position detection. As shown, position sensor 26 is very close the extreme distal end $38_1$, and hence provides very accurate indication of the location of the distal tip, for example, for intra-body navigation.

Elastomeric coating $60_1$ on guidewire $36_1$ has a uniform outside diameter (OD) and smooth outer surface which is particularly useful for delivering cardiac pacing leads, which fit over coating $60_1$ without entanglement. Guidewire $36_1$ further includes a body $90_1$ (e.g., tube). The proximal end of body $90_1$ is ground (i.e., reduced outside diameter) so as to permit mechanical coupling to a proximal connector assembly which provides electrical connectivity between the guidewire (i.e., in particular position sensor 26) and external equipment, such as MPS 24.

Central corewire $52_1$ extends generally from proximal connector assembly (not shown) to the extreme distal plug $58_1$ of guidewire $36_1$. Central corewire $52_1$ provides improved mechanical properties of the guidewire $36_1$. Corewire $52_1$ is configured to distribute bending stresses, tensile loads, and compressive loads over its length, reducing stress on the other components of guidewire $36_1$. In other words, loads (e.g., due to contact with tissue) imposed on shroud $56_1$ are transferred via coating $60_1$ to plug $58_1$ to corewire $52_1$, and similarly loads directly imposed on coating $60_1$ to plug $58_1$ are likewise resolved through corewire $52_1$. Corewire $52_1$ contributes to the overall mechanical properties of the guidewire $36_1$.

Corewire $52_1$ is located substantially at the radial center of guidewire $36_1$. In other words, a central longitudinal axis $66_1$ of corewire $52_1$ is substantially the same as or coincident with central axis "A" of guidewire $36_1$. Corewire $52_1$ has a distal end portion which, in the illustrated embodiment, generally coincides with guidewire distal end $38_1$, and is at least as co-extensive as the axial extent of shroud $56_1$. An extreme distal end $62_1$ of corewire $52_1$ may be flush with or may extend distally a distance $d_1$ past the distal end of the position sensor 26, being situated substantially in the central region of plug $58_1$. In distal end portion, corewire $52_1$ has a circular cross-section of constant diameter.

In an embodiment, corewire $52_1$ may be made of metal, such as stainless steel, titanium, or nickel titanium alloys (i.e., NITINOL), or other biocompatible material. In an embodiment, corewire $52_1$ may be a single continuous wire extending substantially the entire axial length of guidewire $36_1$ (i.e., from proximal connector (not shown) to plug $58_1$), which may provide the benefit of distributing bending stresses over the entire length of guidewire $36_1$. In another embodiment (not shown), corewire $52_1$ may be a multi-piece construction, such as the construction described in U.S. patent application Ser. No. 12/359,010 filed Jan. 23, 2009, to Sela et al., the entire content of which is incorporated herein by reference in its entirety for all purposes and as though fully set forth herein.

The illustrated embodiment of corewire $52_1$ is intended to be exemplary only and not limiting. Many variations could be made to corewire $52_1$ and still fall within the spirit and scope of the present disclosure. For example, corewire $52_1$ may comprise a material other than metal and may have a non-circular cross-section. Additionally, corewire $52_1$ may be solid, hollow, or have some other interior construction. Although an embodiment of a guidewire has been described herein, it will be understood that the position sensors with the core designs described herein may be used in other guidewires without departing from the scope of the disclosure.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples; and, thus, it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A position sensor for a medical device, the position sensor comprising:

a core comprising a body and a first projection extending from the body, the first projection providing a location for an electrical connection, wherein the body is defined by a first diameter and wherein the first projection has an outermost surface that defines a second diameter, wherein the first diameter is equal to the second diameter; and a coil surrounding the body, wherein:
  the coil is configured to generate a voltage when subject to a magnetic field, and
  the first projection comprises a first landing area adapted and arranged for electrical connection of the first projection to a coil lead wire at the location for the electrical connection, wherein the first projection extends proximally from the body and the coil and is configured to concentrate the magnetic field into the coil and increase the voltage.

2. The position sensor of claim 1, wherein the location for the electrical connection on the first projection is located on a surface radially inward of the outermost surface of the second diameter.

3. The position sensor of claim 1, wherein the first projection is integrally formed as part of the core.

4. The position sensor of claim 1, further comprising a conductive element on the first projection, and wherein the coil is electrically connected to the conductive element.

5. The position sensor of claim 4, further comprising an insulating layer between the first projection and the conductive element.

6. The position sensor of claim 1, wherein the first projection further comprises a first side and a second side and wherein a conductive path extends from the first side to the second side.

7. The position sensor of claim 6, wherein the coil is electrically connected to the conductive path.

8. The position sensor of claim 6, further comprising an insulating layer between the first projection and the conductive element.

9. The position sensor of claim 1, wherein the core further comprises an internal lumen extending through the body along a core longitudinal axis.

10. A position sensor for a medical device, the position sensor comprising:
  a core comprising a body and a first projection extending from the body, wherein the core comprises a high-permeability material, the first projection providing a location for an electrical connection; and
  a coil surrounding the body, wherein the coil is configured to generate a voltage when subject to a magnetic field, wherein the first projection extends proximally from the body and the coil, wherein the first projection is configured to concentrate the magnetic field into the coil and increase the voltage, wherein the body is defined by a first diameter and wherein the first projection has an outermost surface that defines a second diameter, wherein the first diameter is equal to the second diameter.

11. The position sensor of claim 10, further comprising a channel in the first projection.

12. The position sensor of claim 10, wherein the core further comprises a second projection extending from the body.

13. The position sensor of claim 10, wherein the location for the electrical connection on the first projection is located on a surface radially inward of the outermost surface of the second diameter.

14. The position sensor of claim 10, wherein the coil further comprises a lead which terminates on the first projection.

15. The position sensor of claim 10, wherein the coil comprises flexible printed circuitry.

16. A medical device configured for diagnosis or treatment of a tissue within a body, the medical device comprising the following:
  an elongate member configured to be received within the body, the elongate member having a proximal end and a distal end; and
  a position sensor disposed within the elongate member proximate the distal end of the elongate member, the position sensor comprising:
    a core comprising a body and first projection extending from the body, the first projection providing a location for an electrical connection between the first projection and a lead wire of the position sensor, wherein the medical device comprises a receptacle into which the first projection is disposed, wherein the body is defined by a first diameter and wherein the first projection has an outer surface that defines a second diameter, wherein the first diameter is equal to the second diameter, the location for the electrical connection on the first projection is located on a surface radially inward of an outer surface of the second diameter;
    a coil surrounding the body, wherein the coil is configured to generate a voltage when subject to a magnetic field; and
    a conductor disposed within the elongate member extending from the position sensor to the proximal end of the elongate member.

17. The medical device of claim 16, further comprising a conductive element on the first projection, and wherein the coil and the conductor are each electrically connected to the conductive element to conduct the voltage induced in the position sensor to the proximal end of the medical device.

18. The medical device of claim 16, further comprising a conductive element on the first projection, wherein the coil is electrically connected to the conductive element, and wherein the medical device comprises a conductive element within the receptacle, and wherein the first projection is adapted to be plugged into the receptacle of the medical device, and wherein the conductive element of the medical device makes electrical contact with the conductive element on the first projection when the first projection is plugged into the receptacle of the medical device.

* * * * *